United States Patent [19]
Olson et al.

[11] Patent Number: 5,916,205
[45] Date of Patent: *Jun. 29, 1999

[54] ABSORBENT INTERLABIAL DEVICE

[75] Inventors: Christy Ann Olson, West Chester; Michael Nyle Hershberger, Cincinnati; Ronald Ray McFall, West Chester; Pamela Jean Brown, Maineville; Thomas Ward Osborn, III, Cincinnati, all of Ohio

[73] Assignee: The Procter & Gamble Company, Cincinnati, Ohio

[ * ] Notice: This patent is subject to a terminal disclaimer.

[21] Appl. No.: 09/031,352

[22] Filed: Feb. 26, 1998

Related U.S. Application Data

[63] Continuation-in-part of application No. 08/979,980, Nov. 26, 1997, and a continuation-in-part of application No. 08/883,606, Jun. 26, 1997, Pat. No. 5,762,644, and a continuation-in-part of application No. 08/876,206, Jun. 16, 1997, and a continuation-in-part of application No. 08/778,520, Jan. 3, 1997, and a continuation-in-part of application No. 08/778,925, Jan. 3, 1997, abandoned, and a continuation-in-part of application No. 08/778,521, Jan. 3, 1997, and a continuation-in-part of application No. 08/706,371, Aug. 28, 1996, Pat. No. 5,885,265.

[51] Int. Cl.[6] .................................................. A61F 13/15
[52] U.S. Cl. ........................ 604/385.1; 604/904; 604/378; 604/330
[58] Field of Search ................................. 604/330, 363, 604/378, 385.1, 904

[56] References Cited

U.S. PATENT DOCUMENTS 3,983,873  10/1976  Hirschman ........................ 604/904
5,336,208  8/1994  Rosenbluth et al. ................ 604/329

*Primary Examiner*—John G. Weiss
*Assistant Examiner*—Dennis Ruhl
*Attorney, Agent, or Firm*—Matthew P. Fitzpatrick; Jeffrey V. Bamber; Jacobus C. Rasser

[57] ABSTRACT

Absorbent devices, and more particularly absorbent devices that are worn interlabially by female wearers for catamenial purposes, incontinence protection, or both, are disclosed. The absorbent interlabial device of the present invention comprises a main absorbent portion with an upper portion, a lower portion opposed to the upper portion, and two ends. The upper portion faces toward the vestibule of the wearer during insertion of the device into the wearer's interlabial space and during use. The ends of the absorbent device are preferably taped so that the lower portion of the interlabial device is longer than the upper portion. The ends are also provided with at least one curvilinear segment, with the ends preferably having a sinusoidal or S-shape. The absorbent interlabial device preferably also has an arcuate pattern of discrete autogenous bonds. The combination of the preferred S-shaped ends and the arcuate bonding pattern provides greater product stiffness control for simultaneous improved comfort and handling characteristics.

4 Claims, 8 Drawing Sheets

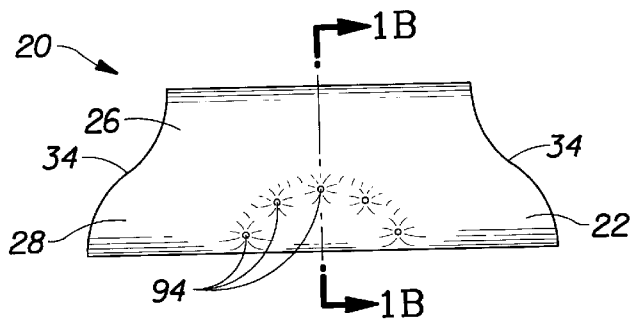
Fig. 1
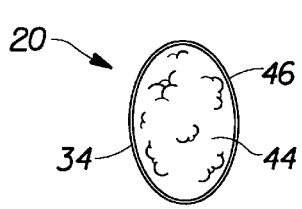
Fig. 1A
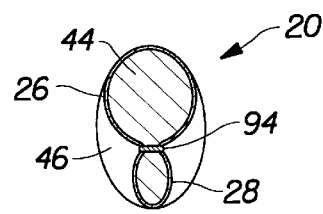
Fig. 1B
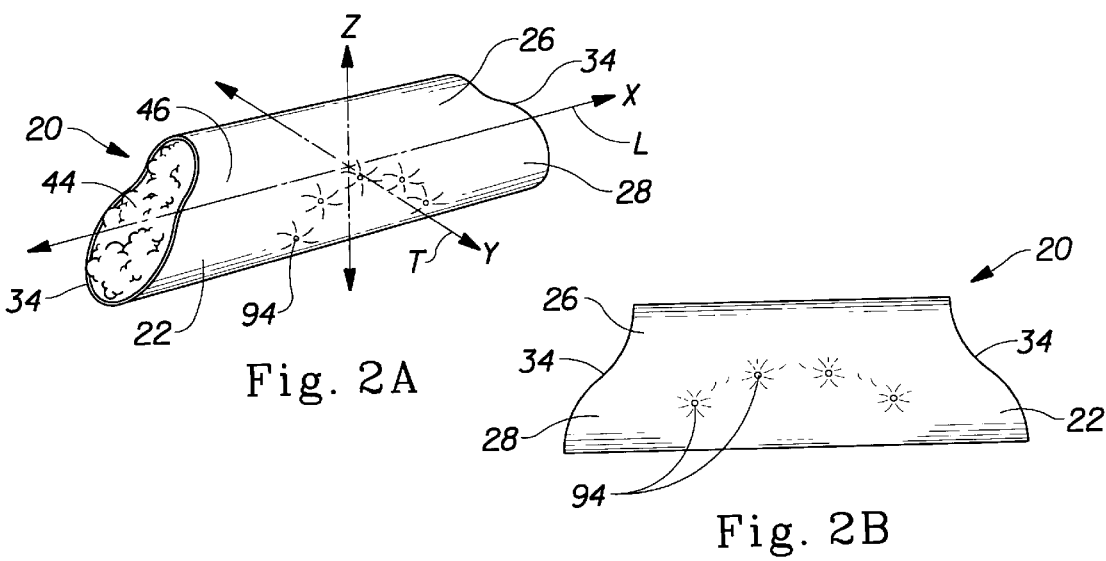
Fig. 2A
Fig. 2B
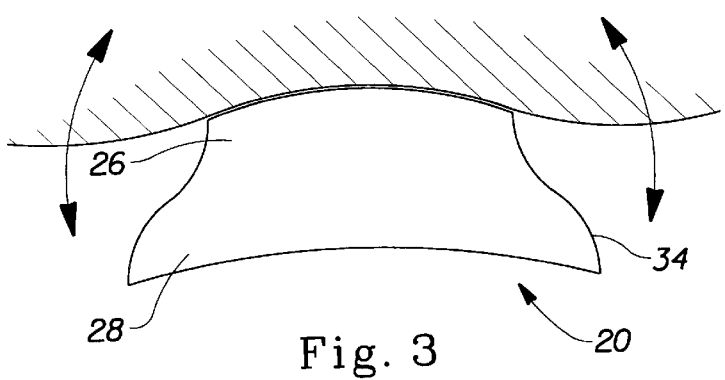
Fig. 3

ABSORBENT INTERLABIAL DEVICE

CROSS REFERENCE TO RELATED APPLICATION

This is a continuation in part of the following: application Ser. No. 08/979,990 filed on Nov. 26, 1997, pending; application Ser. No. 08/883,606 filed on Jun. 26, 1997, now U.S. Pat. No. 5,762,644 application Ser. No. 08/876,206 filed on Jun. 16, 1997, pending; application Ser. No. 08/778,520 filed on Jan. 3, 1997, pending; application Ser. No. 08/778,925 filed on Jan. 3, 1997, now abandoned; application Ser. No. 08/778,521 filed on Jan. 3, 1997, pending; and application Ser. No. 08/706,371 filed on Aug. 28, 1996, now U.S. Pat. No. 5,885,265.

FIELD OF THE INVENTION

This invention relates to absorbent devices, and more particularly to a shaped absorbent device that is worn interlabially by female wearers for catarnenial purposes, incontinence protection, or both.

BACKGROUND OF THE INVENTION

All manner and variety of absorbent articles configured for the absorption of body fluids such as menses, urine and feces are, of course, well known. With respect to feminine protection devices, the art has offered two basic types; sanitary napkins have been developed for external wear about the pudendal region while tampons have been developed for internal wear within the vaginal cavity for interruption of menstrual flow therefrom. Such tampon devices are disclosed in U.S. Pat. No. 4,412,833, entitled "Tampon Applicator", issued to Weigner, et al. on Nov. 1, 1983, and U.S. Pat. No. 4,413,986, entitled "Tampon Assembly With Means For Sterile Insertion", issued to Jacobs on Nov. 8, 1983.

Hybrid devices which attempt to merge the structural features of the sanitary napkins and the tampons into a single device have also been proposed. Such hybrid devices are disclosed in U.S. Pat. No. 2,092,346, entitled "Catamenial Pad", issued to Arone on Sep. 7, 1937, and U.S. Pat. No. 3,905,372, entitled "Feminine Hygiene Protective Shield", issued to Denkinger on Sep. 16, 1975. Other less intrusive hybrid devices are known as labial or interlabial sanitary napkins and are characterized by having a portion which at least partially resides within the wearer's vestibule and a portion which at least partially resides external of the wearer's vestibule. Such devices are disclosed in U.S. Pat. No. 2,662,527, entitled "Sanitary Pad", issued to Jacks on Dec. 15, 1953, and U.S. Pat. No. 4,631,062, entitled "Labial Sanitary Pad", issued to Lassen, et al. on Dec. 23, 1986.

Interlabial pads have the potential to provide even greater freedom from inconvenience because of their small size and reduced risk of leakage. Numerous attempts have been made in the past to produce an interlabial pad which would combine the best features of tampons and sanitary napkins while avoiding at least some of the disadvantages associated with each of these types of devices. Examples of such devices are described in U.S. Pat. No. 2,917,049 issued to Delaney on Dec. 15, 1959, U.S. Pat. No. 3,420,235 issued to Harmon on Jan. 7, 1969, U.S. Pat. No. 4,595,392 issued to Johnson, et al. on Jun. 17, 1986, and U.S. Pat. Nos. 5,074,855 and 5,336,208 issued to Rosenbluth, et al. on Dec. 24, 1991 and Aug. 9, 1994 respectively, and U.S. Pat. No. 5,484,429 issued to Vukos, et al. on Jan. 16, 1996. A commercially available interlabial device is the "FRESH 'N FIT PADETTE" (also known as "IN-SYNC") interlabial pad which is marketed by Athena Medical Corp. (now known as A-Fem) of Portland, Oreg. and described in U.S. Pat. Nos. 3,983,873 and 4,175,561 issued to Hirschman on Oct. 5, 1976 and Nov. 27, 1979, respectively.

Many of these devices have not met with great commercial success, however. There are drawbacks associated with all of the above products. For example, the device described in the Delaney patent does not appear to be capable of an easy and comfortable insertion, due to the possibility of the layers of absorbent material opening up during insertion. The commercially available "PADETTE" interlabial devices suffer from the disadvantage that the blunt edges of the device may cause wearer discomfort. Such blunt edges also increase the tendency of fluids deposited near the edges of the product to run off its edge without being absorbed into the center of the product. U.S. Pat. No. 3,983,873, issued to Hirschman, does describe an interlabial device having tapered ends, but such tapered ends are purely linear. This configuration does increase the surface area presented for absorption as compared to a non-tapered product, but the product of the present invention increases such area even beyond that achievable with the Hirschman device. Additionally, the speed at which the "PADETTE" interlabial device can be manufactured is limited due to its incorporation of stitching with thread. Interlabial devices without flexible extensions may not reliably cover the urethra and/or the vaginal introns during all body movements (e.g. when the wearer is squatting). Such products may also not be reliably expelled when the wearer urinates.

It has been found during development of the present invention that product comfort can be increased by providing an interlabial device with increased stiffness relative to compressive forces in the center of the product, but decreased stiffness relative to such forces near the ends of the product. The stiffer product center contributes to a greater ease of insertion and a better placement of the device within the labia as compared to prior art products. Correspondingly, the greater compressibility (or decreased stiffness) near the ends of the device contributes to greater comfort associated with wearing of the device.

Therefore, a need exits for an interlabial device with shaped edges which increase the total absorbent area of the product facing toward the floor of the vestibule. A need also exists for an interlabial device with a relatively less compressible center and relatively more compressible ends. A need also exists for an interlabial device, which can be manufactured at high speeds with a minimum of waste. A need also exists for an interlabial device that is small in size and that can be easily inserted and that provides protection against incontinence, menstrual discharges, and discharges of bodily exudates throughout a great range of wearer motions. A need also exists for an interlabial device that will reliably be expelled when the wearer urinates. A need also exists for an interlabial device which facilitates sanitary insertion and removal. That is, a need exists for at device which may be inserted into the interlabial space of a wearer while covering the fingertips, thus preventing the fingertips from touching the inside surfaces of the labia.

SUMMARY OF THE INVENTION

This invention relates to absorbent devices, and more particularly to an absorbent device that is insertable into the interlabial space of a female wearer for catamenial purposes, incontinence protection, or both.

The absorbent interlabial device of the present invention comprises a main absorbent portion comprising an upper portion, a lower portion opposed to the upper portion, and two ends. The upper portion faces toward the vestibule floor of the wearer during insertion of the absorbent device into the wearer's interlabial space and during use. That is, the upper portion is positioned furthest inward into the space between the wearer's labia thus leading the lower portion of the absorbent device during insertion. Upon insertion, the lower portion is less fully inserted into the wearer's interlabial space than the upper portion and the lower portion faces away from the floor of the vestibule of the wearer. In a particularly preferred embodiment, the upper portion has a greater transverse direction width (i.e. caliper) than the lower portion along the transverse centerline of the absorbent interlabial device. In such a particularly preferred embodiment, the projected top view width of the interlabial device (the projected view of the inserting edge) is preferably less than the maximum width of the end edges of the device. The ends of the absorbent interlabial device are preferably tapered so that the lower portion of the interlabial device is longer than the upper portion. The ends are also provided with at least one curvilinear segment. In a particularly preferred embodiment of the present invention, the ends of the interlabial device have a sinusoidal shape or "S"-shape. This tapered arrangement with a curvilinear segment exposes the ends of fibers near the ends of the device allowing the exposed fibers to wick liquids deposited near the ends of the device inward toward the center of the device.

The absorbent interlabial device preferably also has a bonding pattern that provides the interlabial device with improved flexibility and a center region that is more resistant to compression than its end regions. The bonding pattern provides bending points for the interlabial device to fit the curvature of the floor of the wearer's vestibule against which the device will be placed. The bonding pattern can also be used to provide the interlabial device with indicia to aid a wearer in properly inserting the interlabial device. Preferably, the bonding also provides an indented portion that serves as a finger gripping region for holding the device during insertion.

The absorbent interlabial device is preferably also includes flexible extensions which extend downwardly and outwardly from the main absorbent portion and are joined to the same. Preferably, the flexible extensions are capable of maintaining contact with inside surfaces of the wearer's labia and covering a substantial portion of the same. The flexible extensions are also preferably capable of covering the wearer's fingertips as the absorbent device is inserted into the interlabial space of the wearer. Preferably, the flexible extensions are capable of maintaining contact with and covering the inside surfaces of the wearer's labia when the wearer's body goes through a range of motions, including squatting. The flexible extensions of the preferred design also block a direct "line of sight" from the outer perimeter of the labia majora to the vaginal introns so that body exudates cannot "miss" the product and the flow of such exudates will be intercepted by the absorbent interlabial device.

In another preferred embodiment, the main absorbent portion comprises a continuous web of material folded into a pleated structure. This structure enhances the surface area available for fluid absorption by allowing fluid to readily penetrate between the pleats of the main absorbent portion.

The present invention relates to a method of making a plurality of absorbent interlabial devices which are symmetrical about a transverse axis and asymmetrical about a longitudinal axis with minimal waste, the method comprising the steps of:

(a) providing a continuous length of absorbent material;

(b) traveling the continuous length of absorbent material in a longitudinal direction;

(c) providing a cover material for at least partially wrapping the continuous length of absorbent material;

(d) at least partially enclosing the continuous length of absorbent material in the cover material so that the cover material lies on opposite sides of the length of absorbent material;

(e) bonding a first portion of the cover material to a second portion of the cover material which lies on the opposite side of the length of absorbent material, the bonding penetrating through the absorbent material and being provided in an alternating pattern wherein in every other application of the bonding pattern, bonds are formed on opposite sides of the longitudinal axis of the length of absorbent material; and (f) making a continuous generally transverse direction cut in the continuous length of absorbent material, wherein the generally transverse direction cut alternates longitudinally across the length of absorbent material to provide a minimum of waste between the interlabial devices.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which like numerals represent like elements throughout and in which:

FIG. 1 is a side view of an absorbent interlabial device having a main absorbent portion with shaped ends and discrete bonding sites.

FIG. 1A is an end view of the absorbent interlabial device shown in FIG. 1.

FIG. 1B is a cross sectional view taken through the transverse centerline of the absorbent interlabial device shown in FIG. 1 along line 1B—1B.

FIG. 2A is a perspective view of the absorbent interlabial device shown in FIG. 1.

FIG. 2B is a side view of an absorbent interlabial device having a main absorbent portion with shaped ends and showing an alternative configuration of discrete bonding sites.

FIG. 3 is a simplified schematic side view of the absorbent interlabial device of the present invention that is formed into a convex configuration when placed against a wearer's body.

DETAILED DESCRIPTION OF THE INVENTION

Figure 4:
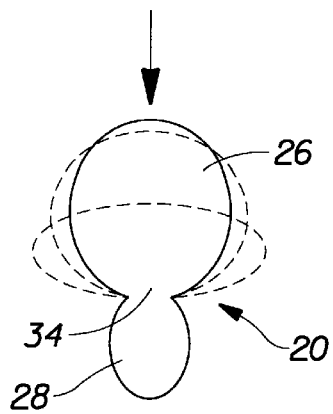
FIG. 4 is an end view of an absorbent interlabial device which shows how the ends flatten when the interlabial device is bent into the configuration shown in FIG. 3.

I. The Absorbent Interlabial Device.

The present invention is directed to an absorbent interlabial device. FIG. 1 shows one embodiment of an absorbent interlabial device, interlabial device 20. The present invention, however, is not limited to a structure having the particular configuration shown in the drawings.

As used herein the term "absorbent interlabial device" refers to a structure which has at least some absorbent components, and which is specifically configured to reside at least partially within the interlabial space of a female wearer during use. Preferably, more than half of the entire absorbent interlabial device 20 of the present invention resides within such interlabial space, more preferably substantially the entire absorbent interlabial device 20 resides within such interlabial space, and most preferably the entire absorbent interlabial device 20 resides within such interlabial space of a female wearer during use.

As used herein, the term "interlabial space" refers to that space in the pudendal region of the female anatomy which is located between the inside surfaces of the labia majora extending into the vestibule. Located within this interlabial space are the labia minor, the vestibule and the principal urogenital members including the clitoris, the orifice of the urethra, and the orifice of the vagina. Standard medical authorities teach that the vestibule refers to the space bounded laterally by the inside surfaces of the labia minora and extending interiorly to the floor between the clitoris and the orifice of the vagina. Therefore, it will be recognized that the interlabial space as defined above may refer to the space between the inside surfaces of the labia majora, including the space between the inside surfaces of the labia minora also known as the vestibule. The interlabial space for purposes of the present description does not extend substantially beyond the orifice of the vagina into the vaginal interior.

The term "labia" as used herein refers generally to both the labia majora and labia minora. The labia terminate anteriorly and posteriorly at the anterior commissure and the posterior commissure, respectively. It will be recognized by those skilled in the art that there is a wide range of variation among women with respect to the relative size and shape of labia majora and labia minora. For purposes of the present description, however, such differences need not be specifically addressed. It will be recognized that the disposition of the absorbent interlabial device into the interlabial space of a wearer as defined above will require placement between the inside surfaces of the labia majora without regard to the precise location of the boundary between the labia majora and the labia minora for a particular wearer. For a more detailed description of this portion of the female anatomy, attention is directed to *Gray's Anatomy*, Running Press 1901 Ed. (1974), at 1025–1027.

The absorbent interlabial device 20 shown in FIGS. 1–2A has a longitudinal centerline L which runs along the "x" axis shown in FIG. 2A. The term "longitudinal", as used herein, refers to a line, axis or direction in the plane of the interlabial device 20 that is generally aligned with (e.g., approximately parallel to) a vertical plane which bisects a standing wearer into left and right body halves when the interlabial device 20 is worn. The terms "transverse," "lateral," or "y direction" as used herein, are interchangeable, and refer to a line axis or direction that is generally perpendicular to the longitudinal direction. The lateral direction is shown in FIG. 2A as the "y" direction. The absorbent interlabial device 20 shown in FIG. 2A also has a transverse centerline T shown in FIG. 2A. The "z" direction, shown in FIG. 2A, is a direction parallel to the vertical plane described above. The term "upper" refers to an orientation in the z-direction toward the wearer's head. "Lower" or downwardly is toward the wearer's feet.

As shown in FIG. 1, the interlabial device 20 comprises at least a main absorbent portion 22 (or "central absorbent"). The main absorbent portion 22 includes an upper portion 26 and a lower portion 28 that is opposed to the upper portion. In use, the upper portion 26 is positioned furthest inward into the wearer's interlabial space. The main absorbent portion 22 also comprises a pair of ends 34 which are tapered (i.e. the ends are farther apart at the lower portion 28 of the device 20 than at the upper portion 26. In addition to being tapered, the ends 34 are provided with at least one curvilinear segment. The main absorbent portion 22 should be at least partially absorbent. The main absorbent portion 22 may comprise non-absorbent portions, such as a liquid impervious barrier to prevent absorbed exudates from leaking out of the main absorbent portion 22.

The interlabial device 20 should be of a suitable size and shape that allows at least a portion thereof to fit comfortably within the wearer's interlabial space and to cover the wearer's vaginal orifice, and preferably also the wearer's urethra. The interlabial device 20 at least partially blocks, and more preferably completely blocks and intercepts the flow of menses, urine, and other bodily exudates from the wearer's vaginal orifice and urethra.

The size of the interlabial device 20 is also important to the comfort associated with wearing the device. In the embodiment shown in FIG. 1, the main absorbent portion 22 of the interlabial device 20 preferably has a length as measured along the top surface of the upper portion 26 of between about 15 mm and about 65 mm. The length of the main absorbent portion 22 of the interlabial device 20, measured along the bottom surface of the lower portion 28 is preferably between about 35 mm and about 120 mm. More preferably, the length of the main absorbent portion of the interlabial device 20, measured along the upper portion 26 is about 35 mm to about 45 mm, most preferably about 38 mm, and the length measured along the lower portion 28 is about 55 mm to about 65 mm, most preferably about 62 mm. The length of interlabial device 20 can also be measured along the longitudinal centerline (at a distance halfway between the top and bottom surfaces of the device). Suitable lengths measured in this manner can include, but are not limited to lengths of 40 mm, 50 mm, and 60 mm. In addition, if desired, a user can use a system of interlabial devices of such varying lengths.

The caliper (or width) of the main absorbent portion 22 of the interlabial device as measured in the transverse direction (or "y"-direction) is preferably less than or equal to about 8 mm, more preferably the caliper is between about 3 mm and about 6 mm, most preferably, the caliper is about 4.5 mm. Caliper measurements given herein were measured using an "AMES" gauge with a 0.25 psi (1.7 kPa) (gauge) load and a 0.96 inch (2.44 cm) diameter foot. Those skilled in the art will recognize that if a 0.96 inch (2.44 cm) diameter foot is not appropriate for a particular sample size, the foot size may be varied while the load on the gauge is accordingly varied to maintain a confining pressure of 0.25 psi (1.7 kPa) (gauge). The height (or "z"-direction dimension) of the main absorbent portion 22 is preferably between about 8 mm and about 35 mm, and more preferably is about 20 mm.

The interlabial device 20 is preferably provided with sufficient absorbency to absorb and retain the exudates discharged from the wearer's body. The capacity of the product, however, is dependent at least partially upon the physical volume of the absorbent interlabial device 20, particularly the main absorbent portion 22 thereof. The main absorbent portion 22 preferably has a capacity of at least about 1 g of 0.9% by weight saline solution, and may have a capacity of up to about. 30 g by using absorbent gels or foams that expand when wet. Capacities may typically range from about 2 to about 10 grams, for saline. Those skilled in the art will recognize that the capacity for absorption of body exudates such as menses will typically be smaller than the capacities given above for absorption of saline. A method for measuring absorbent capacity is described in the Test Methods section, below. Since the interlabial space can expand, larger volumes can be stored in the interlabial space, if the fluid is stored as a gel, which adjusts to the body pressures. Additionally, if the absorbent interlabial device 20 does not reside completely within the wearer's interlabial space, some of the absorbed exudates may be stored externally to the wearer's interlabial space.

The main absorbent portion 22 of the embodiment shown in FIGS. 1–2A may comprise any suitable type of absorbent structure that is capable of absorbing and/or retaining liquids (e.g. menses and/or urine). The main absorbent portion 22 may be manufactured in a wide variety of shapes (as viewed from the side as in FIG. 1 or as viewed from the end as in FIG. 1A). Non limiting examples of shapes for the main absorbent portion when viewed from the end as in FIG. 1A. include ovoid, trapezoidal, rectangular, triangular, cylindrical, hemispherical or any combination of the above. Viewed from the side, as in FIG. 1, the preferred shape for the main absorbent portion 22 is generally tapered with at least one curvilinear segment. In particularly preferred embodiments, the ends 34 of the device 20 have a sinusoidal or "S" shape. In the preferred embodiment shown in FIG. 1, the caliper of the lower portion 28 is smaller than the caliper of the upper portion 26. This relationship is shown more clearly in FIG. 1B, which is a cross sectional view of FIG. 1, taken along the transverse centerline T.

The main absorbent portion 22 may, likewise, be manufactured from a wide variety of liquid-absorbent materials commonly used in absorbent articles such as comminuted wood pulp which is generally referred to as airfelt. Examples of other suitable absorbent materials include cotton fibers or cotton lintels, creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers (in fibrous and particulate form); absorbent gelling materials; or any equivalent material or combinations of materials, or mixtures of these. Preferred absorbent materials comprise folded tissues, cotton batts, woven materials, nonwoven webs, needle punched rayon, and thin layers of foam. The main absorbent portion 22 may comprise a single material. Alternatively, as shown in FIG. 1A, the main absorbent portion 22 may comprise a combination of materials, such as a wrapping layer 46 surrounding a central wadding comprised of an absorbent material 44 (as shown in FIG. 2A).

In the embodiment shown in FIG. 1, the main absorbent portion 22 is formed of a soft absorbent material such as rayon fibers or other suitable natural or synthetic fibers or sheeting. The main absorbent portion 22 shown in FIGS. 1–2A is generally of an ovoid cross sectional shape with tapered ends 34 having at least one curvilinear segment, as shown in FIGS. 1A and 2A. FIGS. 1 and 2A also show the ends 34 of the device 20 having sinusoidal shaped or "S" shaped ends 34.

The ends 34 of the device 20 are tapered and comprise at least one curvilinear segment. In other words, there is at least one segment along the ends 34 where their shape as viewed looking in the "y"-direction is curvilinear. A portion of the ends 34 may present a linear profile, or more than one curvilinear segment may be present. In the embodiment shown in FIG. 1, the ends 34 each have two curvilinear segments oriented in opposite directions. The resulting device 20 shown in FIG. 1 has ends 34 which are sinusoidal or "S"-shaped when viewed from the side (i.e. looking in the "y"-direction) as in FIG. 1.

Providing the device 20 with ends 34 having at least one curvilinear segment, as shown in FIG. 1, endows the absorbent interlabial device 20 of the present invention with several advantages as compared to devices without this feature. Providing the device 20 with tapered ends 34 having at least one curvilinear segment, presents more total absorbent area facing toward the floor of the vestibule as compared to a device with ends oriented vertically in the "z"-direction or with purely linear, tapered ends. The preferred absorbent interlabial device 20 of the present invention improves upon this advantage even further by providing sinusoidal or "S"-shaped ends 34. Such ends 34 present about a 10% increase in surface area oriented toward the vestibule floor as compared to an interlabial device with linear ends (even if such ends are tapered, but without the curvilinear segments provided by the "S"-shape).

The above-described increase in surface area is particularly significant because the exposed ends 34 of the present invention are also the sites of the ends of fibers which comprise the absorbent material 44 which fills the main absorbent portion 22. The ends 34 of the device 20 are, therefore, sites at which deposited fluids (such as bodily discharges) will be wicked toward the interior portion of the main absorbent portion 22 of the absorbent interlabial device 20. Interlabial devices without such tapered ends having a curvilinear segment 34, or in particular, such "S"-shaped or sinusoidal ends 34 are more likely to allow fluids deposited near the longitudinal ends of such a device to run off without being absorbed.

The tapered ends with a curvilinear segment 34, and in particular the "S"-shaped or sinusoidal ends 34, may also provide an increase in the comfort associated with wearing the device 20 as compared to devices with vertical ends. This is particularly true when such "S"-shaped or sinusoidal ends 34 are provided in combination with an arcuate pattern of bonds 94, described in greater detail below.

The main absorbent portion 22 of the embodiment shown in FIGS. 1–2A is preferably shaped so that it comprises an upper portion 26 with a larger transverse sectional dimension relative to that of the lower portion 28. That is, as shown in FIG. 1B, the caliper (or width) of the upper portion 26 is preferably greater than the caliper of the lower portion 28. The upper portion 26 is preferably integral with the lower portion 28. In less preferred embodiments, however, the upper portion 26 and lower portion 28 may comprise separate elements joined together by any suitable means known in the art.

In the embodiment shown in FIGS. 1–2A (and also seen more clearly in FIG. 1B), the juncture of the upper portion 26 and lower portion 28 of the main absorbent portion 22 comprises a substantially abrupt change in the transverse dimension thereby forming a shoulder-like configuration at such juncture. In the embodiment shown in FIGS. 1–2A, the juncture of the upper portion 26 and lower portion 28 of the main absorbent portion 22 is formed by the autogenous bonding method described in more detail below.

In a variation of the embodiment described above and shown in FIGS. 1–2A, the upper portion 26 may have a smaller transverse sectional dimension relative to the transverse sectional dimension of the lower portion 28.

The main absorbent portion 22 can be made by any suitable process. A particularly preferred process for making the main absorbent portion 22 is described in greater detail below. In the embodiment shown in FIGS. 1–2A, the absorbent interlabial device comprises a rayon tow or sliver of core material that is wrapped with a nonwoven web, cover 46. Rayon is typically incompatible with conventional bonding techniques. The autogenous bonding method described below may be used to bond the cover 46 material to itself through the core material 44. Such a bonding method results in the creation of discrete, intermittent bond sites 94 as shown in FIGS. 1–2A.

The intermittent bonds 94 created by the autogenous bonding method described herein may be arranged in any desired pattern. While any suitable number of bonds 94 may be used, preferably the device 20 is provided with between two and eight such bonding sites 94. In a particularly preferred embodiment shown in FIG. 2A, the bonds 94 are arranged in an arcuate pattern in the lower portion 28 where such pattern is symmetrical about the transverse centerline T.

The absorbent interlabial device having the bonding pattern shown in FIG. 2A is more flexible in the direction of the arrows shown in FIG. 3 than a similar interlabial device having a continuous horizontal stitching line. There are several reasons for this. The bonding method of the present invention (described below) can be used to form intermittent bonding patterns which are more flexible than continuous bonding patterns. In addition, by providing a curve in the pattern of bond sites 94, the bond sites 94 act as bending points in order for the absorbent interlabial device 20 to bend so that the upper portion 26 thereof assumes a convex shape as shown in FIG. 3. This would not be possible with a stitching pattern in the form of a continuous straight line. Such a stitching pattern will cause the absorbent interlabial device 20 to kink when an attempt is made to bend it into the configuration shown in FIG. 3.

Figure 5:
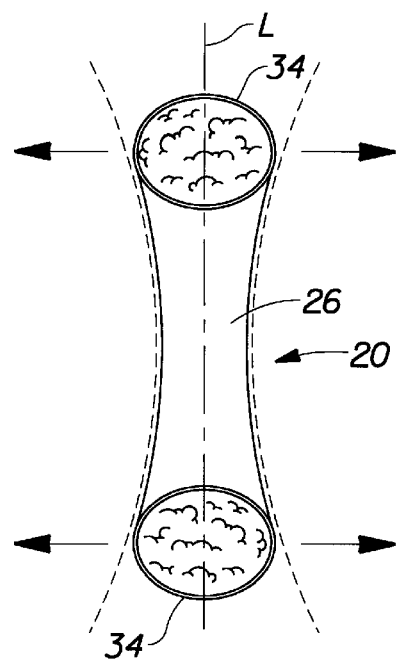
FIG. 5 is a simplified schematic top view of the absorbent interlabial device which shows how the ends of the device widen to fit the configuration of the interlabial space.

The fact that the absorbent interlabial device is able to flex as shown in FIG. 3, is important because this is a shape it will take against the wearer's body when inserted into the interlabial space. The pattern of bonds 94 shown in FIG. 2A, along with the tapered ends 34, also allow the ends 34 of the absorbent interlabial device to flatten as shown in FIG. 4. This provides a more comfortable fit against the adjacent highly sensitive areas of the wearer's body. They also allows the absorbent interlabial device 20 to conform better to the shape of the wearer's body in the interlabial space by widening the ends of the device and narrowing it in the center as shown in FIG. 5.

The use of discrete autogenous bonds 94 provides the absorbent interlabial device 20 with locations of increased absorbent material 44 density. Such high density locations will tend to draw deposited fluids due to wicking action. Therefore, the bonds 94 may be arranged in configurations, such as the arcuate configuration shown in FIG. 2A to draw deposited fluids toward the center of the absorbent interlabial device 20.

The main absorbent portion of the absorbent interlabial device 20 described herein is both flexible and compressible. Flexibility and compressibility are important to product comport. If the absorbent interlabial device 20 (or a component thereof such as the main absorbent portion 22) is too flexible, the device is not conveniently or easily placed between the folds of the labia, if it is too stiff, the device is uncomfortable and when the user is in a sitting position, the product can be forced forward against the clitoris causing discomfort.

The discrete bond sites 94 may be used to control the compressibility of and optimize the compressibility of localized areas of the interlabial device 20. It has been found during development of the present invention that increased product comfort may be obtained by making an interlabial device 20 with a high center to end compressibility ratio. That is, the central portion (i.e. that portion of the device 20 in the vicinity of the transverse centerline T) should be more stiff or less compressible. This stiffness allows for increased ease of insertion of the device 20 and a better placement of the device 20 within the labia. Correspondingly, the end regions (i.e. the portion of the device 20 at or near the ends 34) should be highly compressible or less stiff. This compressibility increases the comfort associated with wearing the device.

The actuate pattern of bond site 94 in conjunction with the S-shaped ends 34 provide the absorbent interlabial device 20 of the present invention with highly compressible ends and a relatively stiff central region. Previous interlabial devices had central regions and ends with the same or nearly the same compressibility (i.e. the center to end compressibility ratio was low). Consequently, the choice of product stiffness was a trade off between ease of insertion on the one hand, and product comfort on the other hand. The present invention, utilizing an arcuate pattern of bonds 94 and S-shaped ends 34 allows for selection of high compressibility at the ends 34 for product comfort simultaneously with the selection of higher stiffness near the transverse centerline T for improved handling and insertion of the device 20.

Compressibility of the absorbent interlabial device 20 is measured using the Compressibility Test described in the Test Methods section, below. Preferably, the interlabial device 20 of the present invention has a bottom center compressibility (as measured using the Compressibility Test, described herein) of at least about 150 grams$_f$, more preferably, at least about 190 grams$_f$, and most preferably, at least about 250 grams$_f$.

The end compressibility (as measured using the Compressibility Test, described herein) of the absorbent interlabial device 20 of the present invention is preferably less than about 50 grams$_f$. Preferably, the center to end compressibility ratio (as described in the Test Methods section, below) is greater than about 4.0, more preferably greater than about 5.0, and most preferably is greater than about 6.0.

The arcuate pattern of bonds 94 shown in FIG. 2A can be used to provide an absorbent interlabial device with an indication of how the device should be held for placement during application. The arcuate pattern of bonds 94 as provides a relatively stiff (with respect to the ends) region for gripping the device 20 for insertion. The arcuate pattern of bonds 94 also provides a visual indication of proper holding of the device 20 for insertion (i.e. the wearer has visual feedback that the upper portion 26 should be first and furthest inserted). In addition to an arcuate pattern, the bonds 94 can be placed in a virtually unlimited number of patterns. These bonds can be used to create products having a virtually unlimited number of possible geometric shapes.

Another particularly preferred embodiment of an absorbent interlabial device 20 of the present invention is shown in FIG. 2B. FIG. 2B shows an absorbent interlabial device 20 with an arcuate pattern of intermittent bonds 94 and S-shaped ends 34. The particularly preferred embodiment shown in FIG. 2B is similar to that shown in FIGS. 1–2A, but various features of the product have been optimized for even more enhanced performance. It has been found during development of the present invention that combination of the various features of the absorbent interlabial device 20 in the manner shown and described with respect to FIG. 2B provides superior product comfort and performance. Nevertheless, it should be noted that not every feature of the absorbent interlabial device 20 of the present invention need be practiced precisely in the manner shown and described with respect to FIG. 2B in order to achieve at least some of the benefits of the claimed invention.

The main absorbent portion 22 of the interlabial device 20 shown in FIG. 2B has a length as measured along the top surface of the upper portion 26 of about 48 mm. The length of the main absorbent portion 22 of the interlabial device 20, measured along the bottom surface of the lower portion 28 is preferably about 72 mm. The lower portion 28 of the absorbent interlabial device 20 shown in FIG. 2B is ideally provided with four discrete bonding sites 94. The use of four bonding sites 94 rather than a greater number (as is shown in FIG. 2A) allow the device 20 to maintain its desired flexibility characteristics while achieving some of the additional benefits described below.

Each of these discrete bonding sites 94 is most preferably spaced about 10 mm apart from each other as measured in the longitudinal direction. Preferably, the bonding sites 94 are symmetrical about the transverse centerline of the device 20. The lower two bonding sites 94 of the device 20 shown in FIG. 2B are located about 6 mm from the bottom surface of the device 20. The upper two bonding sites 94 are located about 10 mm from the bottom surface of the absorbent interlabial device 20.

The particularly preferred embodiment shown in FIG. 2B differs from the preferred embodiment shown and described with respect to FIGS. 1–2A as noted above. Except as so noted, the particularly preferred embodiment shown in FIG. 2B may be, and preferably is, constructed in a manner consistent with the description given above with respect to the preferred embodiment shown in FIGS. 1–2A. The description given above for the embodiment shown in FIGS. 1–2A with respect to acceptable materials, methods of making, and how to use the device 20 are equally applicable to the preferred embodiment shown in FIG. 2B. The advantages described above with respect to the preferred embodiment shown in FIGS. 1–2A resulting from the S-shaped ends 34 being provided in combination with the arcuate pattern of discrete bond sites 94 are also provided by the preferred embodiment shown in FIG. 2B. In addition to these advantages, the preferred embodiment shown in FIG. 2B provides the additional benefit of more completely using the entire capacity of the device 20. In other words, the preferred embodiment of the absorbent interlabial device 20 shown in FIG. 2B will tend to distribute deposited fluid more completely to the ends 34 of the device 20 as the device 20 is loaded. This is because the bond sites 94, which are regions of increased material density as compared to other locations on the absorbent interlabial device 20, are located closer to the ends 34 of the device in the embodiment shown in FIG. 2B as compared to that shown in FIG. 2A. Additionally, the bond sites 94 in the embodiment shown in FIG. 2B are located further from the bottom of the device 20 than those shown in embodiment of FIG. 2A. This feature helps to reduce the fluid transfer to the bottom of the device 20 and helps to reduce the chances of panty soiling resulting from contact of the wearer's panties with the bottom of the device 20 as the device 20 is worn.

The pattern of discrete bonds 94 included on the preferred embodiment shown in FIG. 2B retains the ability to provide indication of how the device 20 should be inserted. The pattern of bonds 94 shown in FIG. 2B, in conjunction with the S-shaped ends 34, also provides the device 20 with highly compressible ends and a relatively stiffer central region (with respect to such ends). It has been found during the development of the present invention that the end compressibility (as measured using the Compressibility Test) of the preferred embodiment shown in FIG. 2B is slightly greater than that associated with embodiments shown in FIGS. 1–2A. Likewise, the bottom center compressibility (as measured using the Compressibility Test) of the preferred embodiment shown in FIG. 2B is slightly less than that associated with the embodiment shown in FIGS. 1–2A. Consequently, the preferred embodiment of FIG. 2B will have a slightly lower center to end compressibility ratio than the embodiment of FIGS. 1–2A. Nevertheless, the preferred ranges of this parameters described above for the embodiment shown in FIGS. 1–2A is still applicable to the preferred embodiment shown if FIG. 2B. It has been found during development of the present invention, that the preferred embodiment shown in FIG. 2B provides a particularly advantageous optimization of localized stiffness and flexibility as well as efficient use of the maximum capacity of the absorbent interlabial device 20.

Figure 6:
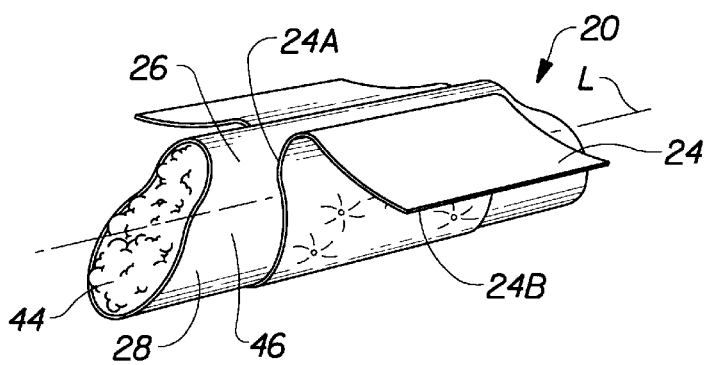
FIG. 6 is a perspective view of an interlabial device according to the present invention which has an optional pair of flexible extensions joined to the main absorbent portion.
Figure 7:
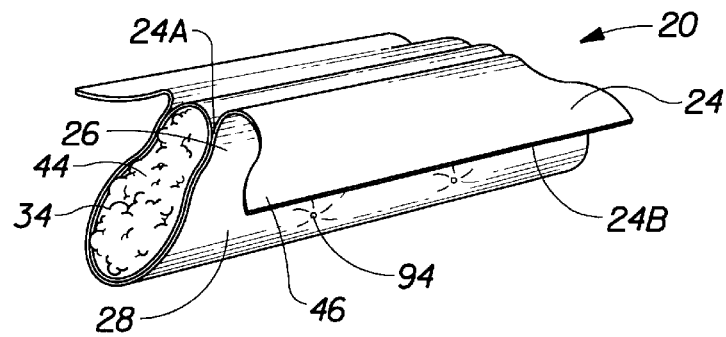
FIG. 7 is a side view of an interlabial device having an optional pair of flexible extensions that have end edges with the same configuration as the ends of the main absorbent portion.

The absorbent interlabial device 20 may also comprise a pair of flexible extensions 24 which are joined to the main absorbent portion 22 of the absorbent interlabial device 20, as shown in FIGS. 6 and 7. In the embodiment shown in FIG. 6, the flexible extensions 24 are generally rectangular in shape. Other shapes are also possible for the flexible extensions 24 such as semi-circular, trapezoidal, or triangular. The flexible extensions 24 may also have the same "S"-shape or sinusoidal shape as the "S"-shaped ends 34 of the absorbent interlabial device 20. Such "S"-shaped or sinusoidal shaped flexible extensions 24 are shown in FIG. 7. The flexible extensions 24 preferably are from about 20 mm to about 160 mm in length, more preferably from about 30 mm to about 130 mm in length, and most preferably from about 40 mm to about 115 mm in length. The flexible extensions 24 can have a length (measured in the x-direction) which is shorter than the main absorbent portion 22, or they can have a length which is the same as or longer than the main absorbent portion 22 of the absorbent interlabial device 20. The width of each flexible extensions refers to the distance from the attachment of flexible extension 24 to the main absorbent portion 22 (or the proximal end 24A of the flexible extension 24) to the distal end (or free end) 24B of the flexible extension 24. The width of the flexible extensions 24 is preferably about equal to or greater than the height of the main absorbent portion as described above. The caliper of the flexible extensions is preferably less than or equal to about 3 mm, more preferably less than or equal to about 2 mm, and most preferably less than or equal to about 1 mm. Ideally, the caliper of the flexible extensions 24 and the main absorbent portion 22 are selected such that the caliper of the overall absorbent interlabial structure 20 is less than or equal to about 8 mm.

The flexible extensions 24 may be constructed of a tissue layer. A suitable tissue is an airlaid tissue available from Fort Howard Tissue Company of Green Bay, Wis., and having a basis weight of 35 lbs./3000 sq. ft. Another suitable airlaid tissue is available from Merfin Hygenic Products, Ltd., of Delta, British Columbia, Canada, having a basis weight of 61 g/m$^2$ and having the designation grade number 176. The flexible extensions 24 may optionally be backed with a layer of material which is impervious or semi-pervious to body exudates such as, polyethylene, polypropylene, or a polyvinylalchohol.

In the embodiments shown in FIGS. 6 and 7 the pair of flexible extensions 24 may comprise a single sheet of material which is wrapped around the entire underside of the device 20 and is attached to the device 20 at least on either side of the longitudinal centerline. The flexible extensions 24 may be both wrapped around the underside of the device 20 as shown in FIGS. 6 and 7 and backed with a layer of material which is impervious or semi-pervious to body exudates, at least in the region of the bottom portion 28 of the device 20. In this manner, the flexible extensions 24 may act as a barrier to protect the body garments of the wearer from becoming soiled when the absorbent interlabial device 20 is worn.

In an alternative configuration, the pair of flexible extensions 24 may comprise separate sheets of material independently joined to the main absorbent portion 22. Preferably, the flexible extensions 24 are arranged symmetrically about the longitudinal centerline L of the main absorbent portion 22. The flexible extensions 24 may be joined to the upper portion 26 of the main absorbent portion 22 of the absorbent interlabial device 20.

The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element; i.e., one element is essentially part of the other element.

The flexible extensions 24 may be joined to the main absorbent portion 22 by any variety of means. For example, the flexible extensions 24 may be joined to the main absorbent portion 22 using any suitable adhesive centered about the longitudinal centerline L of the main absorbent portion 22 (i.e., on opposite sides of the longitudinal centerline L). Such an adhesive may extend continuously along the length of the main absorbent portion 22 or it may be applied in a "dotted" fashion at discrete intervals. Alternatively, the flexible extensions 24 may be joined to the main absorbent portion 22 by stitching (such as with cotton or rayon thread), thermally bonding, fusion bonding, or any other suitable means known in the art for joining such materials.

As shown in FIGS. 6 and 7, the proximal ends 24A of the flexible extensions are attached to the main absorbent portion 22. The flexible extensions 24 extend downwardly and outwardly from the main absorbent portion 22 to a free end 24B which is unattached to the main absorbent portion. The flexible extensions 24 may be biased slightly outward from the main absorbent portion 22 so as to tend to keep the extensions 24 in contact with the inner surfaces of the labia when the absorbent interlabial device 20 is in place. Additionally, the naturally moist surfaces of the labia will have a tendency to adhere to the material comprising the flexible extensions 24 further tending to keep them in contact with the inner surfaces of the labia. Preferably the flexible extensions 24 should be capable of motion from a position where the free ends of the flexible extensions 24 lie adjacent to the main absorbent portion 22 to a position where the flexible extensions 24 extend directly out from the main absorbent portion 22 in the transverse direction (as shown in FIG. 6).

Figure 11:
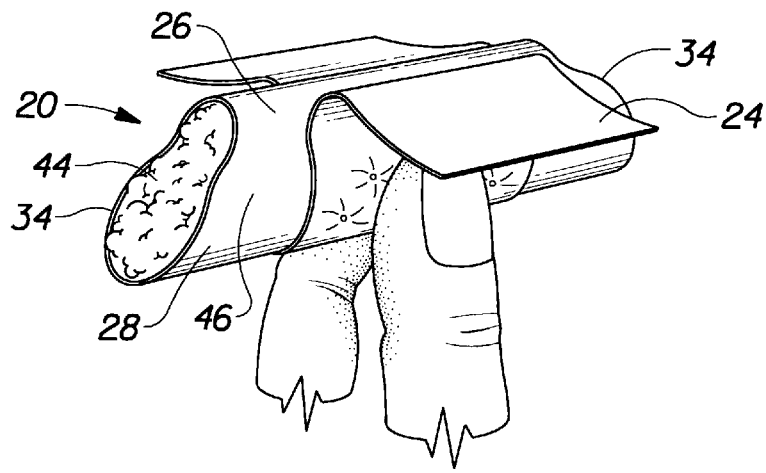
FIG. 11 is a perspective view showing the flexible extensions of the present invention covering the wearer's fingertips as the absorbent device of the present invention is held for insertion into the wearer's interlabial space.

The flexible extensions 24 should be of sufficient width and flexibility to allow the flexible extensions to cover the wearer's fingertips as the absorbent interlabial device 20 is inserted into the wearer's interlabial space. FIG. 11 shows how a wearer may grasp the main absorbent portion 22 of the absorbent interlabial device 20 while the flexible extensions 24 remain between the wearer's fingers and her body as the device 20 is inserted. Additionally, the flexible extensions 24 should be capable of moving with the inner surfaces of the wearer's labia to maintain contact with the same. The flexible extensions 24 help keep the main absorbent portion 22 in place throughout a range of wearer motions such as squatting.

The flexible extensions 24 may be hydrophilic or hydrophobic. The flexible extensions 24 may be treated to make them less hydrophilic than the main portion 22. The hydrophilicity of a material is generally expressed in terms of its contact angle. Thus, the flexible extensions 24 may have an advancing contact angle greater than the advancing contact angle of main portion 22, such that fluid is preferentially directed toward and absorbed by the main portion 22. The flexible extensions 24 may be either absorbent or non-absorbent. Preferably, the flexible extensions 24 have at least some absorbency. The majority of the fluid absorbed and retained by the absorbent interlabial device 20, however, will preferably ultimately be retained in the main portion 22, particularly in the absorbent material 44. For a more detailed description of hydrophilicity and contact angles see the following publications which are incorporated by reference herein: The American Chemical Society Publication entitled "Contact Angle, Wettability, and Adhesion," edited by Robert F. Gould, and copyrighted in 1964; and TRI/Princeton Publications, Publication Number 459, entitled "A Microtechnique for Determining Surface Tension," published in April 1992, and Publication Number 468 entitled, "Determining Contact Angles Within Porous Networks," published in January, 1993, both edited by Dr. H. G. Heilweil.

The strength and stiffness of the flexible extensions 24 are important characteristics of their design. If the flexible extensions 24 have a wet burst strength of about less than or equal to about 15 grams, they will tend to shred and may leave pieces remaining in the wearer's interlabial space. Similarly, if the flexible extensions 24 are as stiff as a manila file folder, they do not provide sufficient flexibility to dynamically adjust to the motion of the labia. The stiffness of the flexible extensions is measured as a bending resistance. Preferably, the flexible extensions 24 have a bending resistance of less than about 25 gm measured using the Three Point Bend Test. More preferably, the flexible extensions 24 have a bending resistance of less than or equal to about 5 gm. A description of the Three Point Bend Test is contained in the Test Methods section, below. The flexible extensions 24 also have an inherent strength, so that during application and wear they do not tear. The wet strength for the flexible extensions should exceed 15 grams, and preferably exceeds 150 grams, and most preferably exceeds 300 grams. The wet strengths given above are measured using the Wet Burst Test which is described in greater detail in the Test Methods section, below.

Figure 8:
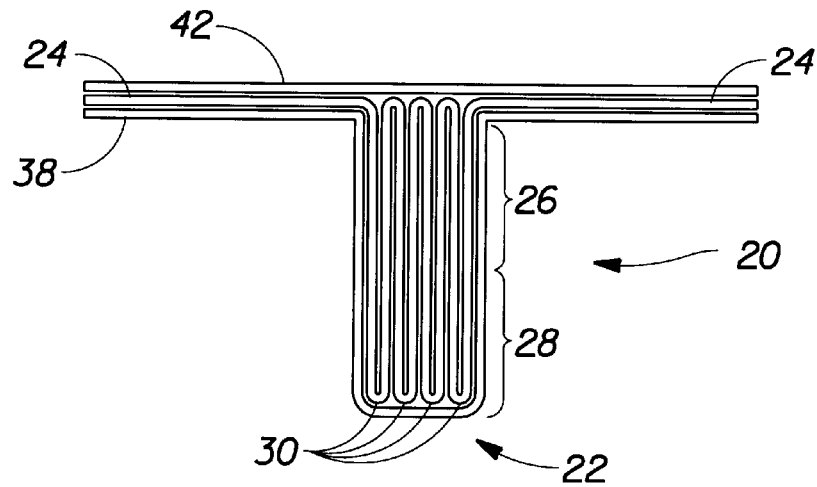
FIG. 8 is an end view of a preferred embodiment of the present invention having a pleated main absorbent portion.

In the embodiment shown in FIG. 8, the main absorbent portion 22 of the absorbent interlabial device 20 comprises a pleated structure. In this embodiment, the main absorbent portion 22 preferably comprises a folded tissue web. The folded tissue web preferably has a strength greater than that of standard non-wet strength toilet tissue. Preferably, the main absorbent portion 22 comprises a tissue having a temporary wet strength of greater than or equal to about 100 g. In a preferred design this wet strength will decay to about 50% or less of the original strength over about 30 minutes.

As shown in FIG. 8, the tissue web comprising the main absorbent portion 22 is folded into a pleated structure comprising a plurality of pleats 30 that are arranged in a laterally side-by-side relationship. The tissue web can be folded so that it has any suitable number of pleats. Preferably, the tissue web is folded so that the overall caliper (i.e., the width) of the main absorbent portion 22 of this embodiment is between about 2 mm and less than or equal to about 7 mm.

The pleats in the folded tissue web are preferably connected or joined (or retained) in some suitable manner so that the pleated sections maintain their pleated configuration, and are not able to fully open. The pleats can be connected by a variety of means including the use of thread, adhesives, or heat sealing tissues which contain a thermoplastic material, such as, polyethylene. A preferred design uses the bonding method described in greater detail below.

The pleated structure of the main absorbent portion 22 provides several advantages. One advantage provided by the pleated structure is that exudates can penetrate into the pleats of the structure which present a larger and more effective absorbent surface for acquisition than a flat surface. This is particularly important when dealing with potentially viscous fluids and particulate material such as cellular debris and clots which can plug the surface of the structure presented to the wearer's body. A second advantage of this design is that the caliper (or width) of the product can be easily and conveniently controlled by varying the number of pleats. The structure shown in FIG. 8 also provides a convenient central zone for grasping the product and inserting into the labia, while the body/fingers on the inserting hand are protected from contacting the wearer's body.

As noted above for the embodiments shown in FIGS. 1–2B, the flexural rigidity of the main absorbent portion 22 is also important for product comfort with the pleated structure shown in FIG. 8. An advantage of the pleated structure is that the number, thickness, and tightness of the pleats control the stiffness of the structure.

The embodiment shown in FIG. 8 preferably has main absorbent portion 22 and flexible extension 24 dimensions similar to those described above for the embodiments shown in FIGS. 1–2B. The width of the main absorbent portion 22 of the interlabial device 20 as measured in the transverse direction (y-direction) is preferably between about 2 mm and less than or equal to about 7 mm. Preferably, in a preferred embodiment, the width of the main absorbent portion of the interlabial device 20 is about 4.5 mm. As shown in FIG. 8, where the main absorbent portion 22 is of a uniform transverse dimension (i.e., there is no abrupt change in transverse dimension defining the juncture between the upper portion and lower portion) the division between the upper portion 26 and lower portion 28 is considered to be at a height equal to about one-half of the total height of the main absorbent portion 22.

The ends 34 of the main absorbent portion 22 of the device 20 shown in FIG. 8 have at least one curvilinear segment and are preferably "S"-shaped or sinusoidal as described above for the embodiment shown in FIG. 1.

The pleated design shown in FIG. 8 has the additional benefit of easily providing the flexible extensions 24. The extensions 24 can comprise the same material as the main absorbent portion 22, or they can comprise a different material. The extensions 24 are joined to the main absorbent portion 22. The extensions 24 may be integral portions of the main absorbent portion 22 (that is, the extensions 24 comprise integral extensions of the absorbent tissue material that is folded to form the main absorbent portion 22.

The main absorbent portion 22 and the flexible extensions 24 of the absorbent interlabial device 20 shown in FIG. 8 may be constructed from any of the materials and be provided with one of the same pattern of bonds previously discussed for the embodiments shown in FIGS. 1–2B.

The embodiment shown in FIG. 8 can be provided with various optional features. For example, there may be spacers or high loft or void zones between the pleats to improve the ability of the device 20 to move exudates downward. Additionally, the pleats on the portion of the product contacting the pelvic floor do not need to be of uniform height. For example, the pleated material in the center might be higher and, therefore, easily collapsed under pressure. Such an arrangement can provide better fit and/or comfort.

In another variation of the pleated structure shown if FIG. 8, the main absorbent portion 22 may comprise a plurality of individual layers joined in a face-to-face relationship. Such a structure may have all of the same characteristics described above for the pleated structure. One benefit of the use of a plurality of individual layers is that the various layers may comprise different materials with different properties or characteristics. Each of the flexible extensions 24 may be integral with one of the individual layers or may be joined separately to the upper portion 26 of the main absorbent portion 22. Preferably, the individual layers are arranged in a side-by-side relationship so that the spaces between the layers are oriented in, the z-direction.

The interlabial device 20 in any of the embodiments shown in the drawings may comprise other optional components. For example, the interlabial device 20 may comprise a topsheet 42 positioned over and joined to all or a portion of its body-facing surface of the device including the flexible extensions 24, and/or a backsheet 38 positioned over and joined to all or a portion of its back surface, including the flexible extensions 24. Preferably, if a topsheet 42 and/or a backsheet 38 is used, these components are joined to at least the main absorbent portion 22. In an alternative embodiment, the main absorbent portion could be at least partially wrapped by a topsheet.

If a topsheet 42 is used, the topsheet should be compliant, soft feeling, and non-irritating to the wearer's skin. Further, the topsheet should be liquid pervious permitting liquids (e.g., menses and/or urine) to readily penetrate through its thickness. A suitable topsheet may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, rayon, polypropylene, or polyethylene fibers) or from a combination of natural and synthetic fibers.

A suitable topsheet 42 for use in the present invention is formed of rayon with a basis weight of about 18 g/m$^2$ and is available from Veratec of Walpole, Mass. This material is particularly suitable for use as a topsheet 42 because it is biodegradable. This material may also be used as an outer cover 46 if an outer cover 46 is desired and a topsheet 42 is not used.

The topsheet may also comprise an apertured formed film. Apertured formed films are pervious to body exudates and, if properly apertured, have a reduced tendency to allow liquids to pass back through and rewet the wearerls skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. The preferred topsheet for the present invention is the formed film described in one or more of the above patents and marketed on sanitary napkins by The Procter & Gamble Company of Cincinnati, Ohio as the "DRI-WEAVE" topsheet.

Another suitable topsheet 30 for the present invention is made in accordance with U.S. Pat. Nos. 4,609,518 and 4,629,643 both issued to Curro et al. on Sep. 2, 1986 and Dec. 16, 1986, respectively. Such a formed film is manufactured by Tredegar Corporation of Terre Haute, Ind.

In a preferred embodiment of the present invention, the body surface of the formed film topsheet is hydrophilic to help liquids transfer through the topsheet faster than if the body surface was not hydrophilic so as to diminish the likelihood that menstrual fluid will flow off the topsheet rather than flowing into and being absorbed by the main absorbent portion 22. In a preferred embodiment, surfactant is incorporated into the polymeric materials of the formed film topsheet. Alternatively, the body surface of the topsheet can be made hydrophilic by treating it with a surfactant such as is described in U.S. Pat. No. 4,950,254 issued to Osborn.

If a backsheet is used, the backsheet could be impervious or semi-pervious to liquids (e.g., menses and/or urine) and is preferably flexible. As used herein, the term "flexible" refers to materials which are compliant and will readily conform to the general shape and contours of the human body. The backsheet prevents the exudates absorbed and contained in the main absorbent portion 22 from wetting articles which contact the absorbent interlabial device 20 such as the wearer's undergarments. The backsheet also assists the main absorbent portion 22 in preventing the wearer's body from being soiled by exudates. Additionally, use of the backsheet may provide an improved surface for the wearer to grasp between the fingers as the absorbent interlabial device 20 is inserted, or as the device is optionally removed with the fingers.

The backsheet may comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). An exemplary polyethylene film is manufactured by Clopay Corporation of Cincinnati, Ohio, under the designation P18-0401. The backsheet may permit vapors to escape from the main absorbent portion 22 (i.e., breathable) while still preventing exudates from passing through the backsheet.

Figure 15:
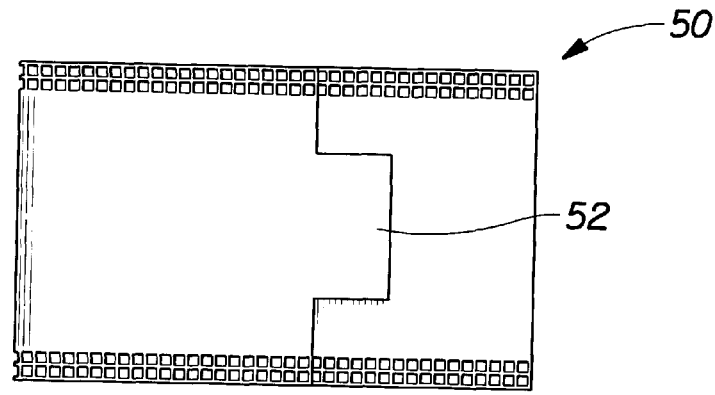
FIG. 15 is front view of an individual package for the interlabial device in an unopened condition.
Figure 16:
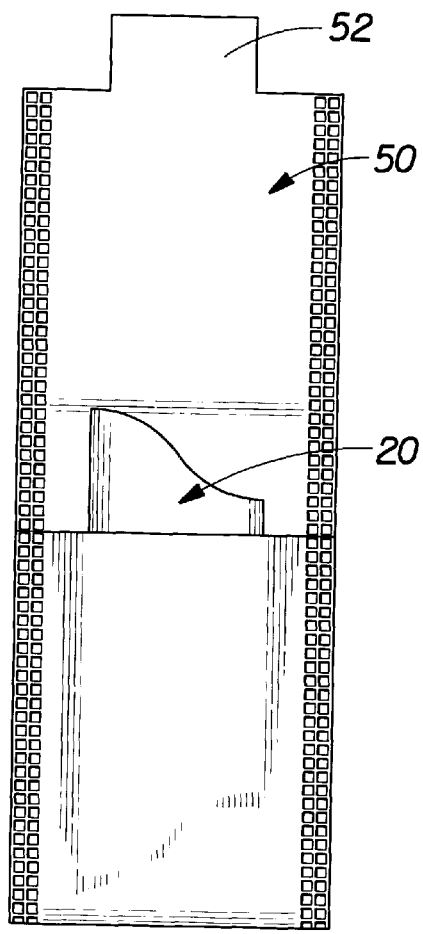
FIG. 16 is front view of the individual package in an opened condition with the interlabial device inside.

If desired, the absorbent interlabial device 20 may be packaged in an individual package, such as the package 50 shown in FIGS. 15 and 16. The individual package 50 may be comprised of a number of suitable materials, including films and flushable materials. In FIGS. 15 and 16, the package 50 is made of a film which is frangible sealed at the edges. The package 50 is provided. with an opening tab 52 which can be of any suitable configuration. Suitable methods for frangible sealing packages are described in U.S. Pat. No. 4,556,146 issued to Swanson and U.S. Pat. No. 5,462,166 issued to Minton, et al. Suitable tabs for such a package U.S. Pat. No. 5,413,568 issued to Roach, et al.

Figure 9:
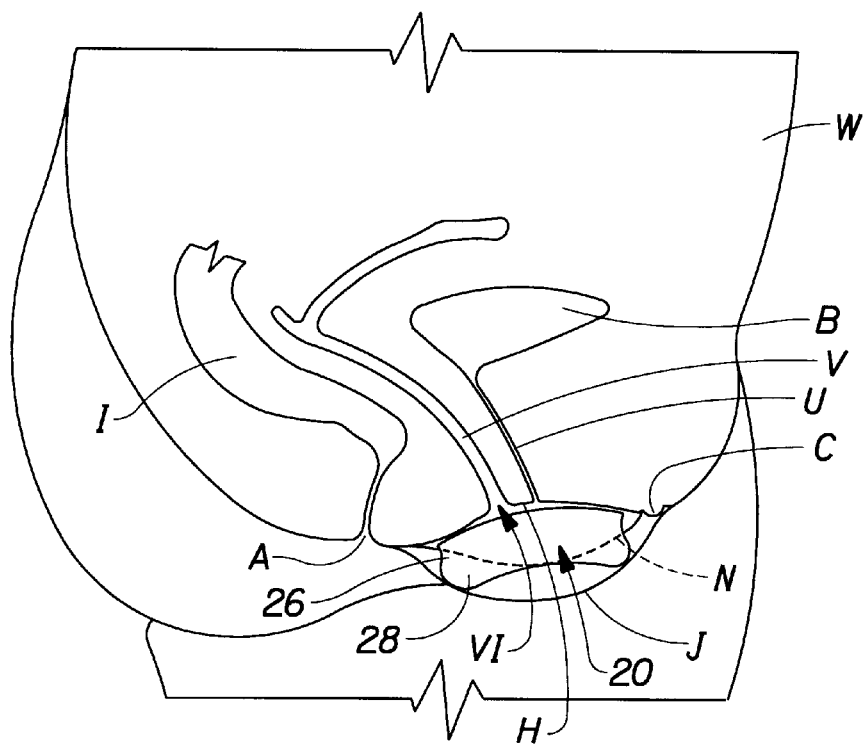
FIG. 9 is a cross-sectional saggital view of a human female wearer showing the placement of the absorbent interlabial device in the wearer's interlabial space.

As previously discussed, the absorbent interlabial device 20 of the present invention is designed to be placed within the interlabial space of a wearer. To use the absorbent interlabial device 20 of the present invention, the wearer holds the main absorbent portion 22 between her fingers. As shown in FIG. 11, the flexible extensions 24 are spread apart so as to cover the tips of the wearer's fingers during insertion. This feature provides for a hygienic insertion of the absorbent interlabial device 20 of the present invention. The interlabial device 20 is inserted with the upper portion 26 inserted first and farthest into the interlabial space. The wearer may assume a squatting position during insertion to assist in spreading the labial surfaces. FIG. 9 shows a preferred embodiment of the absorbent interlabial device 20 of the present invention inserted into the interlabial space of a wearer W. The urogenital members shown in FIG. 9 include the bladder B, the vagina V, the urethra U, the clitoris C, the large intestine I, the anus A, the vaginal introns VI, the hymeneal ring H, the labia minora N, and the labia majora J. FIG. 9 shows the relationship of these anatomical features of the wearer W to the absorbent interlabial device 20 when the device is properly inserted for use. Once the absorbent interlabial device 20 is inserted, the flexible extensions 24 tend to adhere to the inside surfaces of the labia. When the wearer is standing, the labial walls close more tightly around the absorbent interlabial device 20.

The interlabial device 20 is preferably at least partially retained in place by exerting a slight laterally outwardly-oriented pressure on the inner surfaces of the wearer's labia minora, labia majora, or both. Additionally, the product may also be held by attraction of naturally moist labial surfaces to the tissue comprising the flexible extensions 24. Optionally, the flexible extensions 24 or other portions of the device 20 may be provided with a bio-compatible adhesive to assist the adhesion of the device 20 to the inside surfaces of the wearer's labia. The strength of such an adhesive should be selected to assist the absorbent interlabial device 20 in staying in place, while still allowing for reliable, and comfortable removal of the device from the wearer's interlabial space.

The absorbent interlabial device 20 can be worn as a "stand alone" product. Alternatively, it can be worn as a back up to a tampon, or in combination with a sanitary napkin, pantiliner, or incontinence pad for menstrual or incontinence use. If the absorbent interlabial device 20 is used with a sanitary napkin, the sanitary napkin can be of any thickness. Use with a sanitary napkin may be preferred at night to reduce rear soiling. The interlabial device 20 can be worn in conventional panties, or it can be used with menstrual shorts.

Numerous alternative embodiments of the absorbent interlabial device of the present invention are possible. For example, these products are designed to be removed by urination, although an alternative extraction string or loop may be used. These products may also be used with emollients and/or medicinal treatments. For example, a suitable emollient for use on the absorbent interlabial device 20 of the present invention is comprised of about 50% petrolatum, about 39% Cetearyl Alcohol, and about 15% Ceteareth-10. These interlabial products may be constructed of materials which are biodegradable and/or which will fragment in water with agitation (as in a toilet).

Preferably, the absorbent interlabial device 20 of the present invention is toilet disposable. The term "toilet-disposable" as used herein includes the following characteristics of an absorbent interlabial device: flushability, dispersibility, settleability, and biodegradability. As used herein, the terms "flushable" and "flushability" refer to a product's ability to pass through typically commercially available household toilets and plumbing systems without causing clogging or similar problems that can be directly associated with the physical structure of the product. It is recognized, however, that there can be many differences between the various types of toilets available. Therefore, for the purposes of the appended claims, a test to determine the flushability a catamenial product, such as an absorbent interlabial device, is set out in the TEST METHODS section of this specification.

In these or other embodiments, the absorbent interlabial device 20 may be provided with channels or areas of increased absorbent material 44 density. Such regions of increases density may be arranged so as to help direct the flow of bodily fluids toward the center of the device 20 due to the wicking action provided by these density gradients.

The absorbent interlabial device 20 may also be constructed with a plurality of slits in the main absorbent portion 22 so as to permit bending of the product in multiple independent directions. Such a structure allows the product to more easily respond to the stresses associated with body movements.

The top surface of the structure may have one or more slits or have other regions of preferred bending so that product may easily adjust to the vertical pressure against the pelvic floor, to help accommodate the non-linear surface of the pelvic floor between the clitoris and the perineum. The flexible extensions 24 of the absorbent devices above may also act as a spring in both wet and dry conditions such that the sides of the product tend to expand outward pressing against the lateral walls of the labial vestibule, thereby, holding the product in place. In addition, it is preferred that the flexible extensions 24 maintain the ability to act as a "spring" when wet, such as when the product is saturated with liquid. Structures, such as polyurethane foams can provide these properties.

II. Method of Making The Absorbent Interlabial Device.

Figure 10:
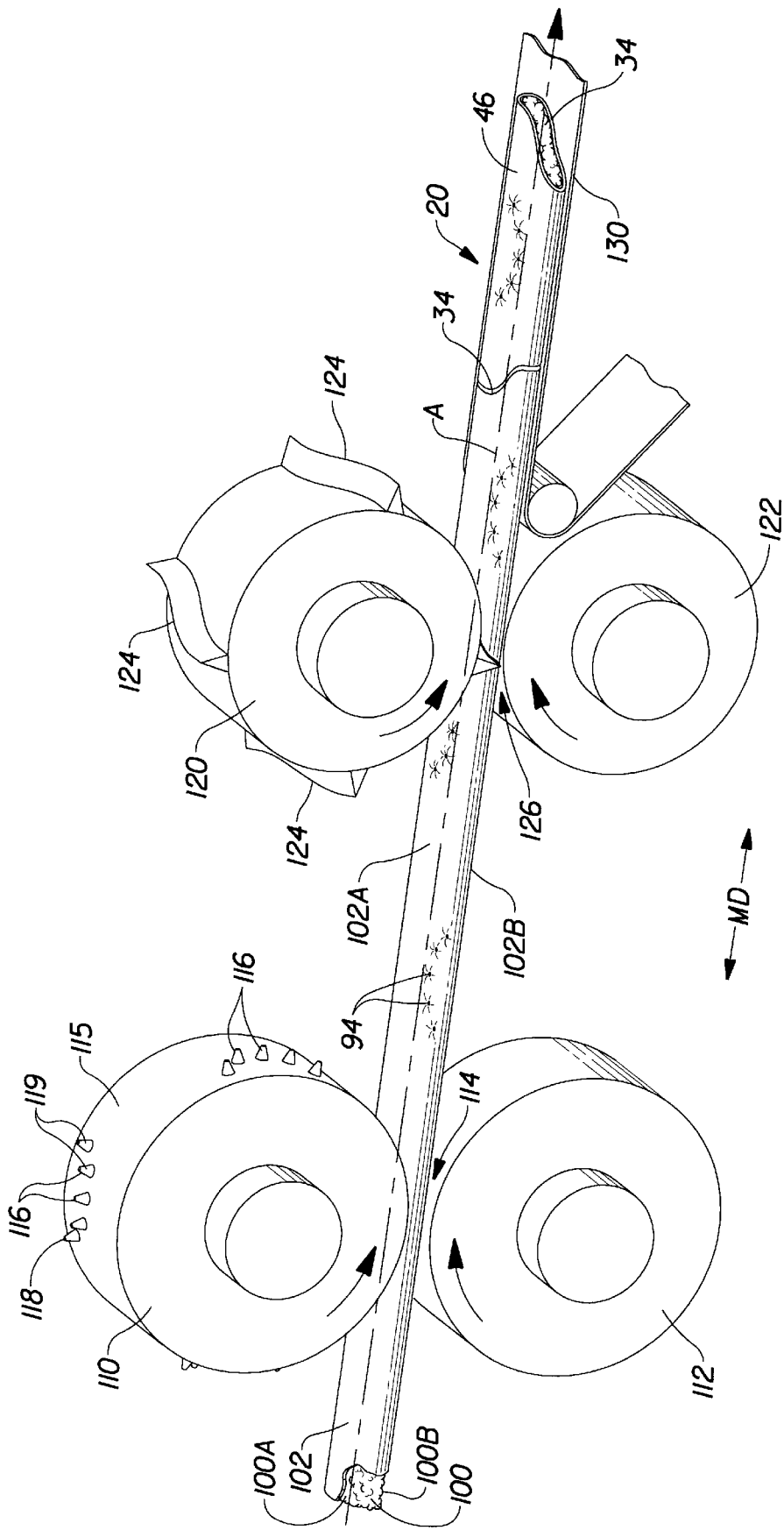
FIG. 10 is a perspective view of the method of the present invention.

FIG. 10 shows a preferred embodiment of a method and apparatus for making the absorbent interlabial device shown in the prior drawing figures.

The method shown in FIG. 10 preferably involves making a plurality of individual absorbent interlabial devices from a continuous length of absorbent material (i.e., a piece of absorbent material having a longer length than width). The absorbent material can be in any suitable continuous configuration. Suitable configurations include, but are not limited to, in the configuration of: discrete cores which may be connected to a continuous web, a web, folded or pleated web, rope, strand, sliver, and tow. In the preferred embodiment shown in the drawings, the absorbent material is provided in the form of a continuous sliver 100.

The continuous sliver of absorbent material 100 is traveling in a longitudinal direction (that is, in the direction of its length dimension). This direction may also be referred to as the "machine direction" or MD. In the embodiment shown in FIG. 10, the sliver of absorbent material 100 is preferably comprised of rayon fibers. The fibers in the sliver 100 are preferably of a discrete length. However, it is also possible (for example, if a tow is used) for the fibers to be continuous length. The fibers in the sliver 100 may be randomly-oriented, or more preferably, generally longitudinally-oriented.

A cover material 102 is provided for the sliver of absorbent material 100. The cover material 102 is preferably also of a continuous length. The cover material 102 preferably comprises at least some thermoplastic material. The cover material 102 can comprise one or more layers of material. Suitable materials are described in the foregoing section of this specification, as the cover 46 or topsheet: 42, and include, but are not limited to, apertured thermoplastic films or webs or nonwovens or the like.

In the particularly preferred embodiment shown, the cover material 102 comprises a polypropylene nonwoven web having a basis weight of 35 g/yd$^2$. One preferred polypropylene nonwoven web is known as Grade 7535660-231 available from Veratec of Walpole, Mass. In alternative embodiments, it may be desirable for the cover material 102 to comprise highly flushable materials such as rayon and cellulose tissues.

As shown in FIG. 10, the continuous sliver of absorbent material 100 is at least partially enclosed within the cover material 102. The cover material 102 preferably at least partially wraps the sliver of absorbent material 100 so that the cover material 102 has portions that lie on opposite sides of the sliver of absorbent material 100. (The sides of the sliver of absorbent material 100, are designated 100A and 100B in FIG. 10.) Preferably, the cover material 102 forms a tube around the absorbent material 100 and completely wraps the absorbent material 100.

The cover material 102 can be formed into a tube around the continuous sliver of absorbent material 100 in any manner known for enclosing a material in a tube of material. There are at least two main ways of forming the tube relative to the sliver of absorbent material 100. The tube can be formed out of the cover material 102 first and the sliver 100 can be inserted into the tube, or the cover material can be formed into a tube around the sliver of absorbent material 100.

In the first type of process, the tube can be formed from the cover material 102 by manipulating the cover material 102 into a cylindrical shape and forming a lap joint or seam on the long edge of the cylinder that is formed. The lap joint may be formed by any suitable bonding means. Suitable bonding means include, but are not limited to adhesives, heat and/or pressure, and ultrasonics. In one preferred embodiment, the lap joint is formed by ultrasonics.

The cylindrical tube is preferably inverted so that the lap joint will be on the inside when formation of the interlabial device is completed. This provides the advantage that the lap joint will not be in contact with the wearer's body when the interlabial device is worn, for improved comfort. Alternatively, the longitudinal side edges of the cover material 102 can be folded inward and bonded so that the lap joint is inside the tube, and there is no need to invert the tube. Methods of forming a tube of material into which an absorbent material is inserted are described in U.S. Pat. No. 4,095,542 issued to Hirschman on Jun. 20, 1978 and U.S. Pat. No. 4,995,150 issued to Gerstenberger, et al. on Feb. 26, 1991.

As discussed above, in an alternative embodiment, the cover material 102 can be formed into a tube by wrapping it at least partially around the sliver of absorbent material 100. In such an embodiment, the cover material 102 can be fed into the process in the machine direction. The cover material 102 can then be folded or wrapped around the sliver of absorbent material 100 in a conventional manner and sealed with a longitudinally-oriented seam. The seam can be formed in any of the manners described above.

As shown in FIG. 10, a first portion 102A of the cover material 102 is preferably bonded through the sliver of absorbent material 100 to a second portion 102B of the cover material. The apparatus used for bonding the covered sliver of absorbent material preferably comprises a pair of cylindrical rolls 110 and 112. Preferably, at least one of the rolls, roll 110, has a relief pattern on its surface. The patterned roll 110 is configured to have a circular cylindrical surface 115, and a plurality of protruberances or pattern elements (or "pattern element segments") 116 which extend outwardly from the surface 115. The relief pattern can be in any suitable configuration. It can be linear, curvilinear, or it can be comprised of linear segments and curvilinear segments. The relief pattern can be continuous or intermittent. The pattern elements 116 can define an unlimited number of patterns and other types of designs. For example, it can define geometric shapes, arrows, words, etc. The land surfaces 118 on the pattern elements 116 can also be provided in a wide variety of possible shapes. Suitable shapes for the land surfaces 118 include, but are not limited to, oval and circular.

The pattern elements 116 have side walls 119 that are preferably not perpendicular with the surface 115 of the cylindrical roll. Preferably, the side walls 119 of the pattern elements 116 form an angle of greater than 45° and less than 90° with surface of the cylindrical roll. Modifying the orientation of the side walls 119 of the pattern elements 116 is necessary due to the thickness of the absorbent material between the materials being bonded, and the desire to avoid tearing the cover material 102.

The relief pattern, in the embodiment of the apparatus shown, comprises a plurality of spaced apart pattern elements 116 having circular land surfaces 118. In the embodiment of the method shown in FIG. 10, the pattern elements 118 are arranged intermittently in a "half moon" configuration. The pattern elements 118 are provided in an alternating pattern so that in every other application of the bonding pattern, bonds 94 are formed on opposite sides of the longitudinal axis, A, of the covered sliver of absorbent material.

The other roll 112, serves as an anvil member and, thus, may be referred to as anvil roll 112. Preferably, the anvil roll 112 is smooth surfaced. In other embodiments, however, both rolls 110 and 112 may have a relief pattern and/or pattern elements thereon. If that is the case, the pattern elements on the opposing rolls are preferably aligned with each other to compress the materials to be bonded therebetween.

The patterned roll 110 and the anvil roll 112 define a pressure biased nip 114 therebetween. The patterned roll 110 and anvil roll 112 are preferably biased toward each other with a pre-determined pattern element loading of from about 20,000 psi (about 140 MPa) to about 200,000 psi (about 1 400 MPa).

The patterned roll 110 and the anvil roll 112 are preferably driven in the same direction at different speeds so that there is a surface velocity differential therebetween. The surface velocity differential preferably has a magnitude of from about 2 to about 40 percent of the roll having the lower surface velocity, more preferably between about 2 to about 20 percent of the roll having the lower surface velocity. The anvil roll 112 is preferably operated at a surface velocity that is greater than the surface velocity of the patterned roll 110. A method of dynamically bonding a laminate between a pair of rolls having a surface velocity differential therebetween is described in greater detail in U.S. Pat. No. 4,854,984 issued to Ball, et al. on Aug. 8, 1989.

The method may further comprise the step of heating one or both of the rolls. If the rolls are heated, they are preferably heated to a surface temperature that is below the melting temperature of the thermoplastic material in the cover material 102. It is also possible, at high line velocities, for the bonding to occur at zero velocity differential (that is, with the nip defining rolls having equal surface velocities).

Parenthetically, for simplicity and clarity of the invention, apparatus 20 is described herein as comprising cylinders 110 and 112. However, cylinders are but exemplary nip defining members. Accordingly, it is not intended to thereby limit the invention to an apparatus comprising cylinders per se. In the same vein, use of the term pattern element is not intended to limit the invention to bonding patterns consisting of only discrete, spaced pattern elements to the exclusion of other patterns: e.g., reticulated patterns or patterns comprising continuous or elongate lines of bonding are also possible.

FIG. 10 shows a particularly preferred bonding process. The bonding process shown in the drawings penetrates through the sliver of absorbent material 100 and autogenously bonds the first portion 102A of the cover material to the second portion 102B of the cover material 102. The term "autogenous", as used herein, refers to bonding without adhesives. The method described herein, however, is not intended to be limited to one which precludes adhesive augmentation of such autogenous bonding. It is also possible to use other types of bonding processes and produce an interlabial device with shaped ends only.

Preferably, however, to produce the interlabial device 20 shown in FIGS. 1–2A, an autogenous bonding process is used. The bonds 94 are arranged in a half-moon shape in an alternating pattern where in every other application of the bonding pattern, bonds 94 are formed on opposite sides of the longitudinal axis, A, of the covered sliver of absorbent material.

The bonding of the first and second portions 102A and 102B of the cover material 102 to each other at least partially encloses and segregates a portion of the covered sliver of absorbent material 100 from another portion of the covered sliver of absorbent material. The bonding causes portions of the cover material 102 that were on opposite sides of the absorbent material 100 to contact each other, and draws the cover material 102 tighter around these portions of the sliver of absorbent material to shape the same.

In this particular embodiment, the bonding makes the portions of the covered sliver of absorbent material that will form the upper portion 26 and lower portion 28 of the finished interlabial device 20 have the desired larger and smaller widths, respectively, as measured along the transverse centerline of the finished product (shown in FIG. 1B). More specifically, the side with bonding will form the lower portion 28 of the interlabial device 20. The half moon bond pattern makes alternating upper and lower portions on opposite sides of the longitudinal axis A of the covered sliver of absorbent material. The bonding, combined with the cutting step described below provides the ability to make an absorbent product that is asymmetrically shaped about its longitudinal axis in both width and in the shape of its ends from a continuous generally symmetrical length of material.

This alternating pattern also has an advantage in processing the covered sliver of absorbent material. If the bonding was all on one side of the longitudinal axis, A, of the covered sliver of absorbent material, this would create a high degree of tension on that particular side of the covered sliver of absorbent material. The alternating pattern equalizes the tension on both sides of the covered sliver of absorbent material so that the bonded covered sliver of absorbent material can be more easily handled and processed.

The bonding process described herein is not limited to embodiments where the bonds are formed completely through the finished absorbent article. For example, in other embodiments, the absorbent material 100 could comprise at least some thermoplastic material, and the cover material 102 could be bonded to the thermoplastic material in the absorbent material 100. In still other embodiments, the bond can be formed through at least a portion of the absorbent material, and the absorbent material can be folded to provide a double, or greater thickness of absorbent material. In such an embodiment, the bond may only penetrate through one or more portions of the absorbent article without penetrating through the entire absorbent article. Numerous other embodiments are possible.

After the bonding process, the covered and bonded sliver of absorbent material is preferably cut to form a plurality of individual absorbent interlabial devices.

The apparatus used for cutting the covered and bonded sliver of absorbent material comprises a pair of rolls 120 and 122. One of the rolls, roll 120, has at least one, and preferably a plurality of knife elements 124 on its surface. The knife elements 124 are preferably configured to make a continuous, generally transverse direction cut in the continuous covered and bonded sliver of absorbent material. Preferably, as shown in FIG. 10, the knife elements are configured to make a sinusoidal cut symmetrically disposed about the longitudinal axis of the covered and bonded sliver of absorbent material.

The other roll 122 serves as an anvil member, and, thus, may be referred to as anvil roll 122. The knife roll 120 and anvil roll 122 also define a nip 126 therebetween.

As shown in FIG. 10, the cutting step provides a generally transverse direction cut that alternates longitudinally across the covered and bonded sliver of absorbent material to cut into individual interlabial devices, and provide a minimum of waste therebetween.

Numerous alternative embodiments of the cutting step described herein are possible. For instance, while the absorbent article described herein has curvilinear end edges, the method of the present invention can be used to make interlabial devices having a broader variety of shaped end edges. For example, in other embodiments, the knife elements can be configured to form absorbent articles having end edges formed by entirely rectilinear segments, entirely curvilinear segments, or partially rectilinear segments and partially curvilinear segments. In addition, while the method of making the interlabial device described herein preferably involves making a fully nested cut so that there is no waste between adjacent interlabial devices, in other embodiment, the knife elements 124 can be configured to make any desired shape cut along the ends of the interlabial devices. Some of these cuts may result in some wasted material being removed between each interlabial device.

The process of the present invention forms a plurality of individual absorbent interlabial devices that are asymmetrical about a longitudinal axis. After the cutting step, the individual interlabial devices 20 can then be sent on a conveyor 130 to a packaging operation for packaging.

If desired, other optional steps can be added to the method shown in FIG. 10. For example, as shown in FIG. 10A, one or more steps may be added in order to make the embodiments with the optional flexible extensions 24 shown in FIGS. 6 and 7.

These additional steps will typically comprise a step of supplying material 134 for optional flexible extensions 24, and a step of adding the material 134 for the flexible extensions to the main absorbent portion 22. The material 134 for the flexible extensions 24 can be added to (that is, brought in and joined to) the main absorbent portion 22 (or more specifically, to the covered sliver of absorbent material that will form the main absorbent portion) in any suitable manner.

Figure 10A:
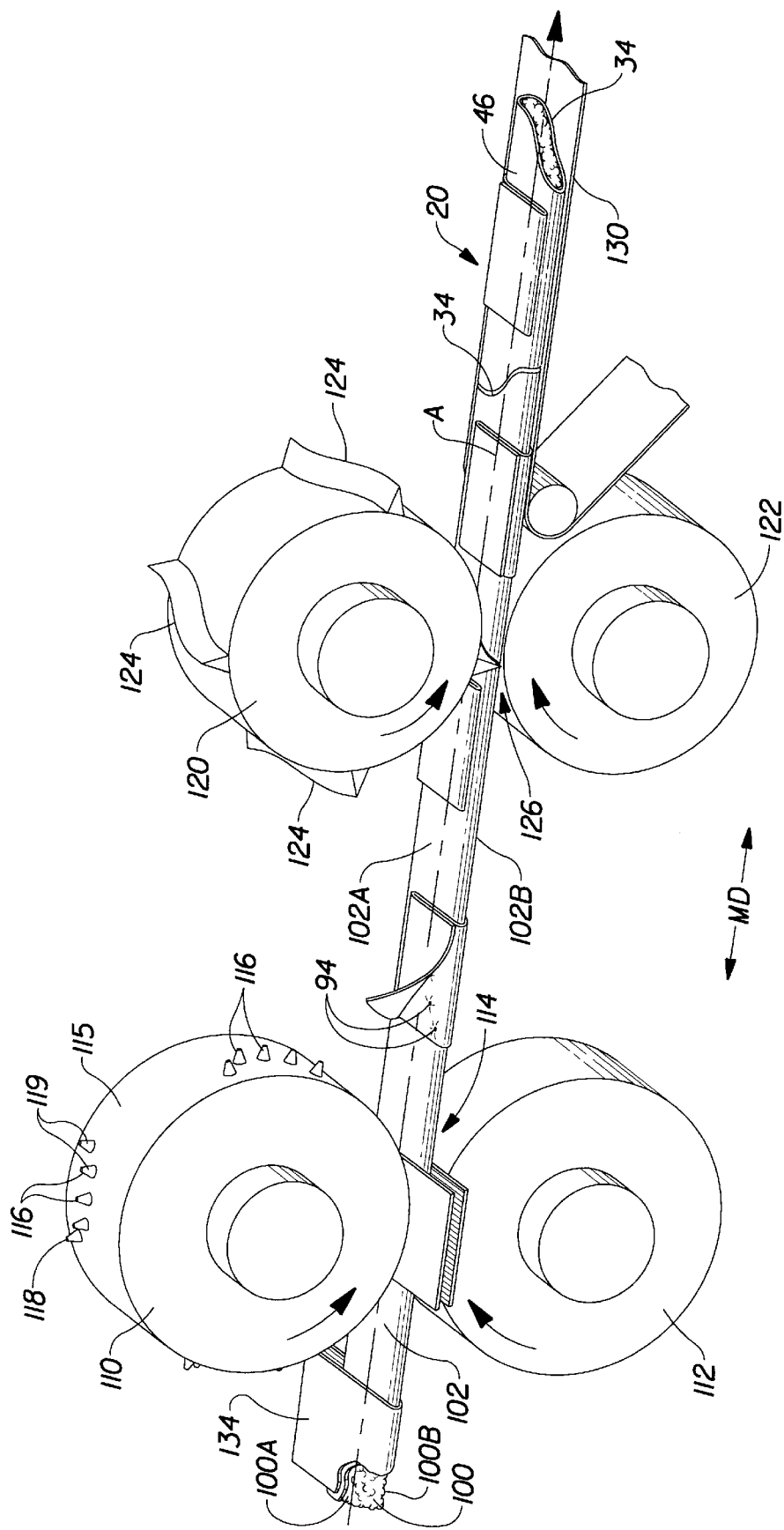
FIG. 10A is a perspective view of an alternative embodiment of the method of the present invention which shows attachment of a pair of flexible extensions to the interlabial device.

The material 134 for the optional flexible extensions 24 can, as shown in FIG. 10A be brought into the process in the form of discrete pieces that have been cut to the desired size of the flexible extensions 24. These discrete pieces are preferably of a size and configuration to be wrapped around the segment of the covered sliver that will form the lower portion of the main absorbent portion to form both flexible extensions 24 as shown in FIGS. 6 and 7. Alternatively, two discrete pieces can be used. These pieces can be attached to each side of the covered sliver to form the flexible extensions 24. In either case, the discrete pieces are then joined to the covered sliver of absorbent material that will form the main absorbent portion of the individual interlabial devices. This can be done in any suitable manner.

For instance, the material 134 for the flexible extensions 24 can be cut and spaced apart slightly using a vacuum roll. In the embodiment shown in FIG. 10A, the cut and spaced apart pieces of material 134 for the flexible extensions 24 are initially held at least temporarily against the covered sliver of absorbent material. This can be done by conventional means such as by wrapping, adhesives, vacuum, and the like. In the embodiment shown, the cut pieces 134 are then permanently joined to the covered sliver of absorbent material.

The cut pieces 134 can be permanently joined to the covered sliver of absorbent material in any suitable manner. Suitable ways of permanently joining the cut pieces 134 to the covered sliver of absorbent material include, but are not limited to adhesives, ultrasonics, and heat and/or pressure bonds. In the particularly preferred embodiment shown in FIG. 10A, the cut pieces 134 are permanently joined to the covered sliver of absorbent material using the same bonding apparatus (rolls 110 and 112) that is used to create bonds 94. As shown in FIG. 10A, this is done simultaneously with the formation of bonds 94.

The cut pieces 134 are then preferably folded into the desired orientation against the covered sliver of absorbent material by a conventional folding mechanism located between the bonding rolls 110 and 112, and the cutting rolls 120 and 122. It is also possible, however, to leave the attached pieces 134 unfolded and to let the consumer fold them to the desired length.

In other alternative embodiments, the material 134 for the optional flexible extensions 24 can be brought into the process in the form of one or more continuous webs that are cut into the flexible extensions 24 after attachment of the continuous web(s) to the covered sliver of absorbent material. In this alternative process, two webs of flexible extension material 134, each of which has a cross-machine direction (CD) width greater than the CD width of the sliver of absorbent material are preferably used. One web will be positioned on top of the sliver of absorbent material and one web will be placed on the bottom of the sliver of absorbent material. The two webs and the sliver of absorbent material could then go through the bonding process used to form bonds 94. In such an embodiment, the continuous web(s) of flexible extension material 134 can be cut at the cutting station simultaneously with the cutting of the bonded covered sliver of absorbent material into individual interlabial devices. This can produce an interlabial device similar to that shown in FIG. 7.

The addition of the flexible extensions 24 can be useful in serving other purposes than simply providing the completed interlabial device with flexible extensions 24. For example, if the cover material 102 was formed into a tube with the lap joint or seam on the outside, the flexible extensions 24 can be useful in covering up the seam on the cover. The flexible extensions 24 may also comprise an impervious material, that may, if wrapped around the underside of the main absorbent portion 22, serve as a liquid impervious barrier in the completed interlabial device as shown in FIG. 7.

Numerous alternative embodiments of the method of the present invention are possible. For example, the method of the present invention is not limited to making interlabial devices having a main absorbent portion 22 formed from a sliver of absorbent material (such as those shown in FIGS. 1–7).

For example, in other embodiments, the main absorbent portion 22 can be made of a continuous tow of absorbent material (that is, a plurality of continuous length fibers). In still other embodiments, the method of the present invention can be used to form interlabial devices having a pleated main absorbent portion, such as the interlabial device shown in FIG. 8. To form a pleated interlabial device, instead of the continuous sliver of absorbent material, a folded web which comprises absorbent material is fed into the apparatus shown in FIG. 10.

In other embodiments, the method of the present invention can be varied to provide absorbent interlabial devices with unique features. For example, where the interlabial devices are made from a tube of absorbent material wrapped by a cover material, the lap joint used to bond the cover material in a cylindrical configuration may be altered to vary the properties of the interlabial device.

For instance, the lap joint can be in the form of a continuous bond, or intermittent bonds. Either of these types of bonds may be in the form of straight lines, curved lines, arcuate lines, sinusoidal lines, or any other suitable configuration. A continuous straight line lap joint will provide a plain cylindrical tube. However, forming the lap joint with intermittent bonds may provide a more comfortable lap joint, should the lap joint come into contact with the wearer's body. The dynamic bonding method described in U.S. Pat. No. 4,854,984 issued to Ball, et al. can be used to form a lap joint with intermittent bonds, or bonds in any other desired configuration.

Forming the lap joint with a sinusoidal bonding pattern can be used to provide the cylindrical tube of absorbent material with alternating regions of greater and lesser diameter. The points of the lap joint where the sine wave has a maximum amplitude (relative to the interior of the absorbent material) will form a region where the tube has a greater diameter. The points of the lap joint where the sine wave has a minimum amplitude will form regions where the tube has a lesser diameter. A sinusoidal lap joint may, thus, form a "caterpillar-like" cylindrical structure. This can produce interlabial devices with additional bending axes which make the interlabial devices very flexible in their longitudinal dimension.

In embodiments where the lap joint is formed by the process described in the Ball, et al. patent, the lap joint formation process can be combined with a cutting process to remove excess material outboard of the lap joint. Such a combination of bonding by pressure and/or heat with cutting may be termed "fusion/slitting".

In addition, the bonding pattern used to bond through and shape the interlabial device can be modified to provide the interlabial device with regions of differing (e.g., greater) density to wick liquids to specific predetermined portions of the device. Providing wicking lines in an interlabial device is believed to be more effective than providing them in absorbent pads such as sanitary napkins. Interlabial devices, due to the fact that they will remain in the wearer's interlabial space during use, cannot vary in their position relative to a wearer's body to the extent result, which can. As a result, wicking lines and channels will remain in the desired position relative to the wearer's body, and will more reliably move bodily exudates in the direction(s) desired.

The method described herein provides many unique benefits. As discussed above, the method described herein provides the ability to make an absorbent product that is asymmetrically shaped about its longitudinal axis both in width and in the shape of its ends from a continuous generally symmetrical length of absorbent material. The method described herein is capable of making such alternating asymmetrically shaped products with little or no waste between adjacent products.

The method described herein also has particular advantages when compared to sewing processes. A sewing process is very slow, and unsuitable for use on high speed manufacturing lines, and would be the speed limiting part of the entire process. The method of the present invention, on the other hand, can be used on a manufacturing line running at high speeds (e.g., 700–1,000 feet per minute), which is not possible with stitching processes. The method of the present invention is also capable of forming an unlimited number of possible bond patterns, and is not limited to forming continuous, generally straight line bonds, as are sewing processes.

Test Methods

Absorbent Capacity

Absorbent capacity may be determined as follows. The test is performed on samples that have been conditioned by leaving them in a room at 50% relative humidity and at 73° F. for a period of two hours prior to the test. The test should be performed under similar conditions.

The article is weighed to the nearest 0.1 gram. The article is then submerged in a beaker of sterile 0.9% saline solution (obtainable from the Baxter Travenol Company of Deerfield, Ill.), such that the article is totally submerged and is not bent or otherwise twisted or folded. The article is submerged for 10 minutes. The article is removed from the saline and laid horizontally on a wire mesh screen having square openings 0.25 inches by 0.25 inches (0.64 cm by 0.64 cm) for five minutes to allow the saline to drain out to the article. Both sides of the article are then covered with absorbent blotters, such as the filter paper #631 available from the Filtration Science Corp., Eaton-Dikeman Division of Mount Holly Springs, Pa. A uniform 17.6 grams per square centimeter load is placed over the article to squeeze excess fluid out. The absorbent blotters are replaced every 30 seconds until the amount of fluid transferred to the absorbent blotters is less than 0.5 grams in a 30 second period. Next, the article is weighed to the nearest 0.1 gram and the dry weight of the article is subtracted. The difference in grams is the absorbent capacity of the article.

Three Point Bend Test

The Three Point Bend Test is performed on samples that have been conditioned by leaving them in a room at 50% relative humidity and at 73° F. for a period of two hours prior to the test. The test should be performed under similar conditions.

Figure 12:
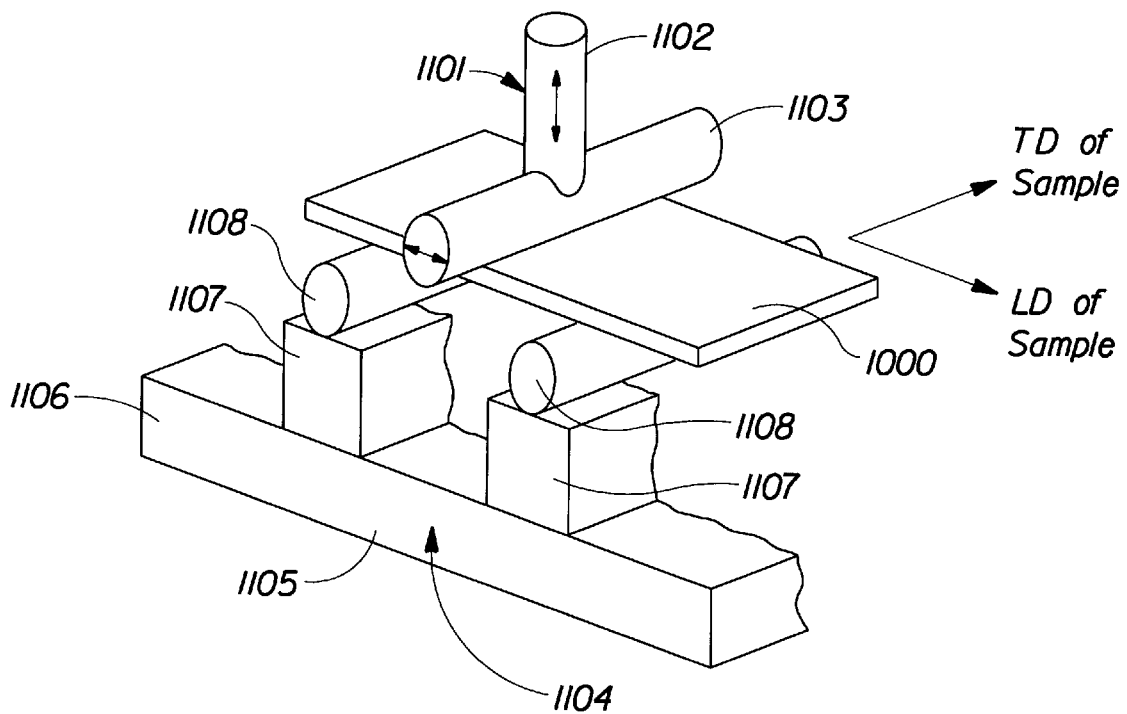
FIG. 12 is a schematic perspective view of the Three Point Bend Test apparatus.

The three point bend test uses an INSTRON Model 4502 tensile and compression testing machine, which is available from Instron Corporation of Canton, Mass. A 10N load cell is used and is attached to the INSTRON machine in accordance with the manufacturer's instructions. The test also, uses a special displacement "T-rod" and a special test sample holder. As shown in FIG. 12, the "T-rod" 1101 comprises a pair of 6.40 mm diameter metal rods perpendicularly mounted together. The drive rod 1102 is about 125 mm long and the push rod 1103 is about 75 mm long. Preferably, the end of the drive rod 1102 is tapered to fit the circumference of the push rod 1103 and the two are glued, welded and/or screwed to each other. The opposite end of the drive rod 1102 is mounted to the crosshead unit of the INSTRON machine. The test sample holder 1104 comprises a fixture base 1105 for positioning and supporting a pair of supporting rods 1108. The fixture base 1105 comprises a base 1106 and two rectangular supports 1107 mounted in parallel on the base 1106. The base 1106 and the supports 1107 are each preferably made of LEXAN (plexiglas) plate of about 10 mm to about 13 mm thickness. A supporting rod 1108 of the same materials as the "T-bar" and about 150 mm long is mounted on each support 1107 of the fixture base 1105. The supporting rods 1108 are mounted so as to leave 10 mm of open space between them (measured at the point on each rod which is closest to the other). As shown in FIG. 12, the "T-rod" 1101 is centered between the supporting rods 1108.

The INSTRON machine is set for a crosshead speed of 2.0 in/min (50.8 mm/min). The INSTRON machine is set up so that the crosshead unit will travel 10 mm down and back for each sample tested.

Prior to testing of a sample, the T-rod 1101 is lowered until it is resting directly on top on one of the supporting rods 1108. The vertical position of the Trod 1101 is "zeroed" when the load as it rests on supporting rod 1108 is about 1 $gram_f$. The T-rod 1101 is then raised 5 mm from this zero position and centered between both supporting rods 1108.

The sample 1000 to be tested is a piece of material taken from one of the flexible extensions. The sample 1000 taken from the flexible extensions should have a dimension of about 25 mm in the longitudinal direction LD and a dimension in the transverse direction of a about 10 mm. The sample is placed so that the push rod 1103 is running parallel to a side of the sample that was oriented in the transverse direction TD.

The T-rod 1101 is then allowed to travel through a complete 10 mm cycle (i.e., 10 mm down and 10 mm back up). Consequently, the T-rod 1101 will make contact with the sample 1000 after about 5 mm and bend the sample about an additional 5 mm. The bending resistance is the peak force required to bend the sample as the T-rod travels through a complete 10 mm cycle.

Compressibility Test

Overview

The Compressibility Test is performed on samples that have been conditioned by leaving them in a room at 50% relative humidity and at 73° F. for a period of two hours prior to the test. The test should be performed under similar conditions.

The compressibility test uses an INSTRON Model 4502 tensile and compression testing machine, which is available from Instron Corporation of Canton, Mass. A 10N load cell is used and is attached to the INSTRON machine in accordance with the manufacturer's instructions. The test also uses the same displacement "T-rod" described above for the Three Point Bend Test and a conventional plate-type vice as a sample holder.

The sample holder is a standard vice comprising a pair of plates whose faces are disposed opposite each other. The plates should be longer and higher than the sample to be tested.

The compressibility test may be performed on an absorbent interlabial device 20 made according to the specification above. The product to be tested may have flexible extensions or may be made without such flexible extensions. The testing routine consists of first measuring the bottom center compressibility, then measuring the end compressibility of each end. Finally, the top center compressibility of each product is measured. The bottom center compressibility and the average compressibility of the ends are used to compute the center to end compressibility ratio.

Test Procedure

1. The product to be tested is first placed within the vice with the upper portion between the plates of the vice and the lower portion (i.e. the bottom) sticking out free above the plates of the vice. The device should be placed within the vice such that about 15 mm is left protruding above the top surface of the plates of the vice. The tightness of the vice should be sufficient to hold the product firmly so that it will not slip, but need not be significantly tighter than necessary to hold the product in place. A confining pressure of about 1 psi is suitable.
2. The INSTRON machine is set for a crosshead speed of 2.0 in/min (50.8 mm/min). The INSTRON machine is set up so that the crosshead unit will travel 5 mm down and 5 mm back for each sample tested. The sample is placed as described above, such that the push rod 1103 will push down about midway along the length of the sample (i.e. along the transverse centerline, on the bottom of the product) tending to compress it.
3. Prior to testing of a sample, the T-rod 1101 is lowered until it is resting directly on top of the sample. The length of the rod 1101 is perpendicular to the length of the sample. The vertical position of the T-rod 1101 is "zeroed" when the load as it rests on supporting rod 1108 is about 1 $gram_f$. The T-rod 1101 is allowed to travel through a complete 5 mm cycle (i.e., 5 mm down and 5 mm back up). Consequently, the T-rod 1101 will be in continuous contact with the sample during its stroke and will compress the sample about 5 mm. The compression resistance is the peak force required to compress the sample as the T-rod travels through a complete cycle (i.e. 5 mm down and 5 mm back up).

4. Record the bottom center compressibility as the peak force required to compress the sample as described in Step #3 when the push rod 1103 is oriented to compress the bottom of the device along its transverse centerline.
5. Without removing the product from the vice, adjust the positioning of the sample relative to the T-rod 1101 such that the push rod 1103 will now compress one end of the sample about 5 mm from the end edge. The push rod 1103 should still be oriented in the transverse direction, although it is no longer oriented above the transverse centerline. "Zero" the position of the push rod 1103 above the sample as described above in Step #3. Let the T-rod 1101 complete a cycle of 5 mm down stoke and 5 mm up stroke. Record the peak force as the first end compressibility.
6. Repeat the procedure of Step #5 for the other end of the sample. Record this peak force as the second end compressibility.
7. Average the first and second end compressibility results. Record this value as the end compressibility.
8. Take the ratio of the bottom centerline to the end compressibility (i.e. divide the bottom center compressibility from Step #4 by the end compressibility of Step #7). Record this value as the center to end compressibility ratio.
9. Remove the product from the vice and replace it as described in Step #1 except that about 15 mm from the top of the device should be left protruding from the top of the plates of the vice.
10. Repeat steps 2, 3, and 4 as described except that the T-rod 1101 will be compressing the top of the device along the transverse centerline. Record this result as the top center compressibility.
11. Repeat the entire test sequence (steps 1–10) with at least 5 different samples of the same type.

Burst Strength Test

Overview

A test specimen, held between annular clamps, is subjected to increasing force that is applied by a 0.625 inch diameter, polished stainless steel ball. The burst strength is that force that causes the sample to fail. Burst strength may be measured on wet or dry samples.

Apparatus

Burst Tester

Intelect-II-STD Tensile Test Instrument, Cat. No. 1451-24PGB or the Thwing-Albert Burst Tester are both suitable. Both instruments are available from Thwing-Albert Instrument Co., Philadelphia, Pa. The instruments must be equipped with a 2000 g load cell and, if wet burst measurements are to be made, the instruments must be equipped with a load cell shield and a front panel water shield.

Conditioned Room

Temperature and humidity should be controlled to remain within the following limits:
Temperature: 73±3° F. (23° C.±2° C.)
Humidity: 50±2% Relative Humidity
Paper Cutter
Scissors or other equivalent may be used
Pan
For soaking wet burst samples, suitable to sample size
Solution
Water for soaking wet burst samples should be equilibrated to the temperature of the conditioned room.

Timer
Appropriate for measuring soak time
Sample preparation

1) Cut the sample to a size appropriate for testing (minimum sample size 4.5 in ×4.5 in). If the sample to be tested is too small (e.g., a flexible extension with overall dimensions less than 4.5 in ×4.5 in) a larger sample of the same material should be used to determine wet burst strength. Prepare a minimum of five samples for each condition to be tested.
2) If wet burst measurements are to be made, place an appropriate number of cut samples into a pan filled with temperature-equilibrated water.

Equipment Setup
1) Set the burst tester up according to the manufacturer's instructions. If an Intelect-II-STD Tensile Test Instrument is to be used the following are appropriate:
Speed: 12.7 centimeters per minute
Break Sensitivity: 20 grams
Peak Load: 2000 grams
2) Calibrate the load cell according to the expected burst strength.

Measurement and Reporting
1) Operate the burst tester according to the manufacturer's instructions to obtain a burst strength measurement for each sample.
2) Record the burst strength for each sample and calculate an average and a standard deviation for the burst strength for each condition.
3) Report the average and standard deviation for each condition to the nearest gram.

Report the average and the standard deviation for each group of four samples.

Flushability Test

Overview

As noted above, the terms "flushable" or "flushability" refer to a product's capacity to pass through typical commercially available household toilets and plumbing drainage systems without causing clogging or similar problems that can be directly associated with the physical characteristics of the product. For the purpose of the appended claims, catamenial products are evaluated for flushability via relative ease of toilet bowl and trap evacuation and subsequent transport through a simulated plumbing system. The flushability of such a device should be measured by the following test procedure.

The test procedure is designed to simulate two days of normal toilet usage for a family of 4 (2 men, 2 women). The test employs a flushing sequence to simulate the following conditions: male urination visits, female urination visits (including post urinary drying with tissue), disposal of catamenial product (that is, the interlabial device or other device to be tested) with cleaning using tissue, and bowel movement visits. The amount of tissue to be used for each tissue flush is a normal loading of 2 strips of seven sheets. The normal loading is based on consumer research regarding typical habits and practices. The test is designed to simulate the conditions a product will encounter if it is flushed through a conventional toilet and into a municipal sewer or into a septic tank. Samples are evaluated for: 1) toilet bowl and trap clearance, 2) drain line blockage, and 3) disintegration during flushing.

Apparatus

Figure 13:
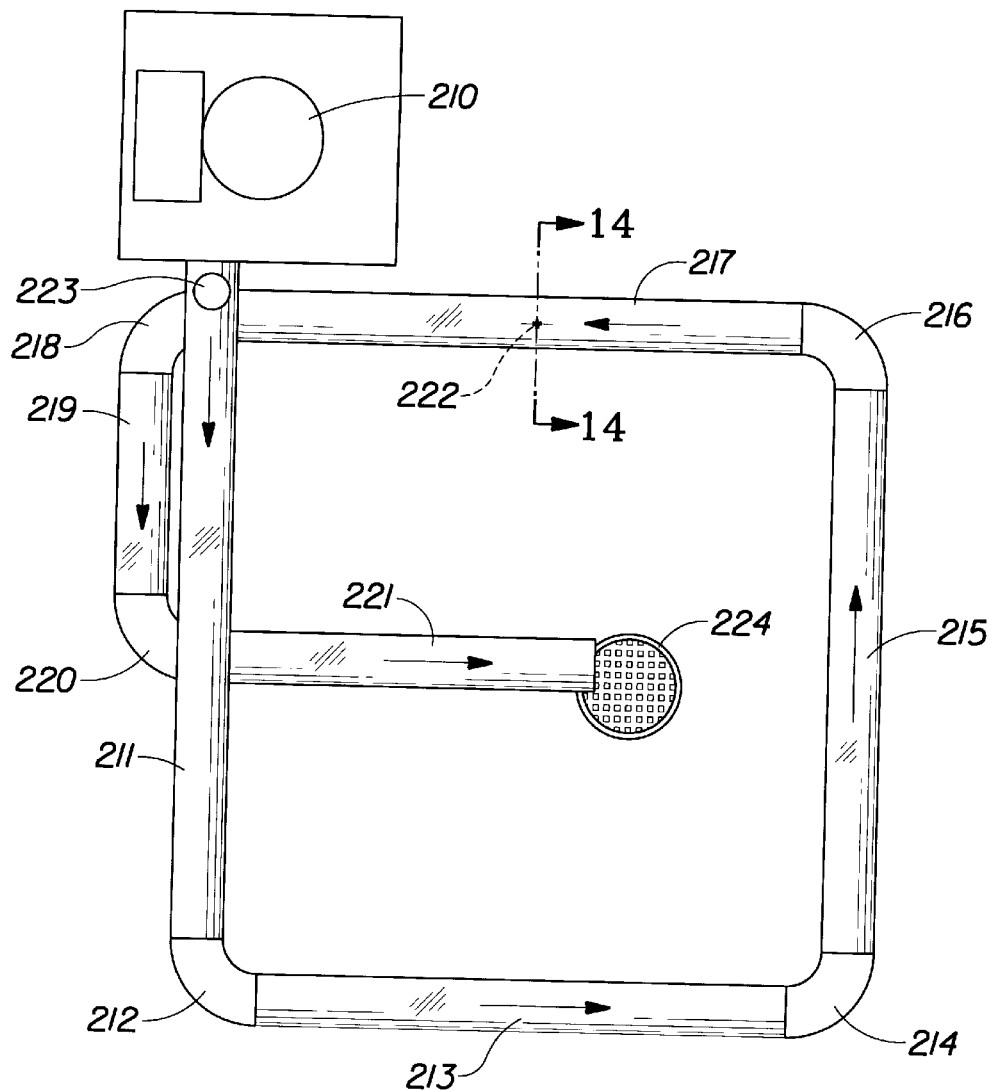
FIG. 13 is a plan view of an apparatus suitable for the flushability determination according to the method described in the TEST METHODS section, below.
Figure 14:
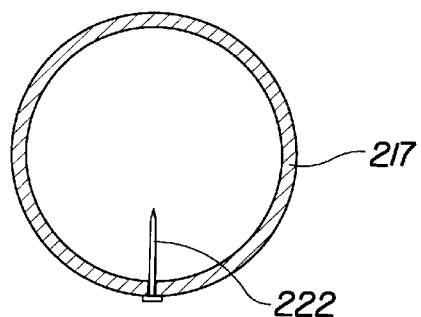
FIG. 14 is a cross-section of the flushability apparatus of FIG. 13 taken along line 14—14 thereof.

An apparatus suitable for the flushability test is shown in plan view in FIG. 13. The apparatus includes:

a 3.5 gallon (13.2 liter) water saver siphon vortex toilet referred to as 210 (additional toilets can also be attached to the piping layout shown in FIG. 13 to evaluate the behavior of test samples using different flushing mechanisms such as commercial, pressure toilets);

approximately 59 feet (18 meters) of 4 inch (10 cm) inside diameter acrylic pipe (As can be seen from FIG. 13, the piping is assembled in roughly a square configuration having linear runs 211, 213, 215, 217, 219, 221 approximately 10 feet (3 meters) long);

a cast iron tee 223 slightly downstream of the toilet 210 that is open to the atmosphere for venting;

five cast iron ninety degree elbows 212, 214, 216, 218, and 220;

a snag (simulated obstruction) 222 positioned vertically (FIG. 14) approximately 15 feet from the pipe's terminal end and approximately 1 inch (2.5 cm) long; and a screen 224 (No. 4 Tyler sieve) to capture solid effluent for evaluate apparatus ration.

The apparatus used for this method is set up to be equivalent to ANSI Standard A112.19.2M-1990 for Vitreous China fixtures. The piping is plumbed to provide a drop of 0.25 inch per foot (2 centimeters/meter) of pipe length.

Materials

Tissue Product used in Test: standard "CHARMIN" toilet tissue manufactured by The Procter & Gamble Company of Cincinnati, Ohio.

Synthetic Fecal Material: Prepared according to the method described below.

Test Flushing Sequence

The test flushing sequence simulates 2 days of normal toilet usage for a family of 4 (2 men, 2 women; based on consumer habits and practices research). The sequence of 34 total flushes consists of 14 flushes with an empty bowl, 8 flushes with tissue only, 6 flushes with tissue and a catamenial product and 6 flushes with tissue and simulated fecal matter (SFM). When it is used, the SFM is placed in the bowl just prior to the addition of tissue. The SFM loading of 160 g±5 g consists of two 1 inch (2.5 centimeter)×4 inch (10 centimeter) pieces and one 1 inch (2.5 centimeter)×2 inch (5 centimeter) piece. Folded tissue strips (or the catamenial product) are placed in the bowl at 10 second intervals. Ten seconds after the final strip or catamenial product is placed into the bowl, the toilet is flushed. The flushing sequence is described below as a series of two routines combined in the following order:

Routine #1 (To be performed first 6 times for a total of 30 flushes)

1) Flush With Tissue Only—Take a drain line blockage reading 2 minutes after the water reaches the simulated obstruction, wait 1 additional minute, and move to step 2.

2) Flush With Empty Bowl. Take a drain line blockage reading 2 minutes after the water reaches the snag point and move to step 3.

3) Flush With Tissue and Catamenial Product—Take a drain line blockage reading 2 minutes after the water reaches the snag point, wait 1 additional minute, and move to step 4.

4) Flush With Empty Bowl. Take a drain line blockage reading 2 minutes after the water reaches the snag point and move to step 5.

5) Flush With Tissue and Simulated Fecal Matter (SFM). Take a drain line blockage reading 2 minutes after the water reaches the snag point, wait 1 additional minute.

Routine #2 (To be performed 1 time)

1) Flush With Tissue Only—Take a drain line blockage reading 2 minutes after the water reaches the snag point, wait 1 additional minute, and move to step 2.

2) Flush With Empty Bowl. Take a drain line blockage reading 2 minutes after the water reaches the snag point and move to step 3.

3) Flush With Tissue Only—Take a drain line blockage reading 2 minutes after the water reaches the snag point, wait 1 additional minute, and move to step 4.

4) Flush With Empty Bowl. Take a drain line blockage reading 2 minutes after the water reaches the snag point.

Total number of flushes per sequence is 34.

If, after the second flush in the flushing sequence, the product remains in the bowl or trap after flushing, the tissue and or catamenial product is plunged into the drainage line manually and the flushing sequence will continue. After completion of each trial loading, the drainage pipe will be cleared prior to beginning subsequent testing.

The above described flushing sequence is repeated three times for each test product.

Data Reporting

The degree of drain line blockage is determined by measuring the length of water dammed up behind the obstruction. Graduations are marked every 12 inches (30 centimeters) on the drainpipe upstream of the obstruction. Each one foot length that the water is backed up corresponds to 0.25 inch (0.6 centimeter) or 6.25% of blockage at the obstruction point. Test product residues which exit the drainpipe are also collected.

The following data are recorded for each evaluation:

1) Incidence of failure (%) of catamenial product to clear bowl and trap in one flush 2) Incidence of failure (%) of catamenial product to clear bowl and trap in two flushes 3) Incidence of product on simulated snag 4) Maximum level (%) of drain line blockage 5) Cumulative level (%) of drain line blockage over the 2 day simulated test period.

Preferably, the products described herein will completely clear the bowl at least about 70% of the time in two or fewer flushes, more preferably at least about 80% of the time in one flush, even more preferably at least about 90% of the time in one flush, and most preferably at least about 95% of the time in one flush. The products described herein will preferably have a maximum level of drain line blockage of less than or equal to about 80%. The products described herein will preferably have a cumulative level of drain line blockage over the 2 day simulated test period of less than or equal to about 50%.

Preparation of Synthetic Fecal Material

I. Materials Needed:

Feclone synthetic fecal matter (900 grams); (Available from Silicone Studio, Valley Forge, Pa. as product BFPS-7 dry concentrate )

Tap water at 100° C. (6066 grams)

II. Equipment Needed:

Mixer (Available from Hobart Corp., Troy, Ohio as Model A200)

Extruder (Available from Hobart Corp., Troy, Ohio as Model 4812)

Disposable Centrifuge tubes with screw caps (50 ml) (Available from VWR Scientific, Chicago, Ill. as Catalog No. 21-008-176)

Water Bath to control temperature to 37° C.

III. Preparation:

1. Pour the 100° C. water into the mixing bowl of the mixer and add the dry Feclone concentrate.

2. Mix on low for 1 minute.
3. Mix on medium speed for 2 minutes.
4. After the material is well mixed, transfer to the extruder.
5. Using an ice pick, punch a small hole in the tip of each centrifuge tube.
6. Extrude the Feclone into the centrifuge tubes.
7. Cap the centrifuge tubes and store in the refrigerator.
8. Before using, put the tubes in the water bath at 38° C.

This concludes the test.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

What is claimed is:

1. An absorbent device insertable into the interlabial space of a female wearer, said absorbent device having a length, a width, and a height, said length, width, and height being oriented in an x-direction, a y-direction, and a z-direction, respectively, said absorbent device comprising:

a main absorbent portion having an upper portion, a lower portion, two spaced apart longitudinal ends, an absorbent material, and an outer cover for said absorbent material, said cover at least partially wrapping said absorbent material; wherein
    said length of said main absorbent portion is greater than said height of said main absorbent portion,
    said length of said upper portion of said main absorbent portion is shorter than said length of said lower portion of said main absorbent portion,
    said ends of said main absorbent portion when viewed from the side of said main absorbent portion have at least one curvilinear segment,
    said absorbent material is penetrated by autogenous bonds that join one portion of said cover to an opposing portion of said cover, and
    said autogenous bonds are discrete bonds arranged in an arcuate pattern.

2. The absorbent device of claim 1 wherein said ends of said main absorbent portion when viewed from the said of said main absorbent portion are S-shaped.

3. The absorbent device of claim 1 comprising four of said discrete autogenous bonds.

4. The absorbent device of claim 1 wherein said absorbent device tends to distribute deposited fluid substantially to the ends of the device prior to said device reaching its absorption capacity.

* * * * *